US012807961B2

(12) United States Patent
Coisman

(10) Patent No.: US 12,807,961 B2
(45) Date of Patent: Nov. 24, 2026

(54) METHODS FOR MANUFACTURING VIRAL VECTORS

(71) Applicant: Regeneron Pharmaceuticals, Inc., Tarrytown, NY (US)

(72) Inventor: Brent Julian Coisman, Cambridge, MA (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 1017 days.

(21) Appl. No.: 18/009,239

(22) PCT Filed: Jun. 10, 2021

(86) PCT No.: PCT/US2021/036840
§ 371 (c)(1),
(2) Date: Dec. 8, 2022

(87) PCT Pub. No.: WO2021/252782
PCT Pub. Date: Dec. 16, 2021

(65) Prior Publication Data

US 2023/0212591 A1 Jul. 6, 2023

Related U.S. Application Data

(60) Provisional application No. 63/037,777, filed on Jun. 11, 2020.

(51) Int. Cl.

| | |
|---|---|
| ***C12N 15/64*** | (2006.01) |
| ***B01D 61/02*** | (2006.01) |
| ***B01D 61/14*** | (2006.01) |
| ***C07K 1/16*** | (2006.01) |
| ***C07K 1/34*** | (2006.01) |
| *A61K 48/00* | (2006.01) |

(52) U.S. Cl.
CPC ........... *C12N 15/64* (2013.01); *B01D 61/029* (2022.08); *B01D 61/149* (2022.08); *C07K 1/16* (2013.01); *C07K 1/34* (2013.01)

(58) Field of Classification Search
CPC . C12N 15/64; C07K 1/16; C07K 1/34; B01D 61/149; B01D 61/029
See application file for complete search history.

(56) References Cited

U.S. PATENT DOCUMENTS

| | | | | |
|---|---|---|---|---|
| 12,018,293 | B2 * | 6/2024 | Hong | C12N 7/00 |
| 2004/0167320 | A1 | 8/2004 | Couto et al. | |
| 2005/0260672 | A1 | 11/2005 | Couto et al. | |
| 2012/0219588 | A1 | 8/2012 | Thompson et al. | |
| 2015/0360180 | A1 | 12/2015 | Lutz et al. | |
| 2015/0361129 | A1 | 12/2015 | Natarajan et al. | |
| 2016/0074774 | A1 | 3/2016 | Cvetkovic et al. | |
| 2017/0002332 | A1 | 1/2017 | Boudeffa et al. | |
| 2017/0173537 | A1 | 6/2017 | Gagnon | |
| 2019/0099702 | A1 | 4/2019 | Steen et al. | |

FOREIGN PATENT DOCUMENTS

| | | | | |
|---|---|---|---|---|
| CN | 104395341 | A | 3/2015 | |
| CN | 105378074 | A | 3/2016 | |
| CN | 105745009 | A | 7/2016 | |
| CN | 105980571 | A | 9/2016 | |
| CN | 106457153 | A | 2/2017 | |
| JP | 2013-507141 | A | 3/2013 | |
| JP | 2016-512700 | A | 5/2016 | |
| JP | 2017-503486 | A | 2/2017 | |
| WO | 2014/145578 | A1 | 9/2014 | |
| WO | 2015/133972 | A1 | 9/2015 | |
| WO | 2016/033546 | A1 | 3/2016 | |
| WO | 2019/199476 | A1 | 10/2019 | |
| WO | 2019/236811 | A1 | 12/2019 | |
| WO | 2020/037249 | A1 | 2/2020 | |
| WO | WO-2020191369 | A1 * | 9/2020 | C12M 29/10 |
| WO | 2021/252782 | A1 | 12/2021 | |

OTHER PUBLICATIONS

Dizon-Maspat et al. Single pass tangential flow filtration to debottleneck downstream processing for therapeutic antibody production. Biotechnology and Bioengineering 109:962-970; (Year: 2011).*
Landau et al., Packaging system for rapid production of murine leukemia virus vectors with variable tropism. J Virol. Aug. 1992;66(8):5110-3.
Manufacturing Chemist, Single-pass tangential flow filtration: A versatile approach to streamlining biomanufacturing. Retrieved online at: https://www.manufacturingchemist.com/news/article_page/Single-pass_tangential_flow_filtration_a_versatile_approach_to_streamlining_biomanufacturing/155874. 10 pages, Jun. 28, 2019.
Soneoka et al., A transient three-plasmid expression system for the production of high titer retroviral vectors. Nucleic Acids Res. Feb. 25, 1995;23(4):628-33.
International Search Report and Written Opinion for Application No. PCT/US2021/036840, dated Sep. 15, 2021, 7 pages.

* cited by examiner

*Primary Examiner* — Quang Nguyen
(74) *Attorney, Agent, or Firm* — McCarter & English, LLP; Marcie B Clarke; Dylan M. Blumenthal

(57) ABSTRACT

The present disclosure provides improved systems and methods for purifying and/or concentrating lentiviral compositions.

19 Claims, 5 Drawing Sheets

METHODS FOR MANUFACTURING VIRAL VECTORS

CROSS REFERENCE TO RELATED APPLICATIONS

This application is a National Stage application under 35 U.S.C. § 371 of International Application No. PCT/US2021/036840, filed Jun. 10, 2021, which claims the benefit under 35 U.S.C. § 119 (e) of U.S. Provisional Application No. 63/037,777, filed Jun. 11, 2020, which is incorporated by reference herein in its entirety.

BACKGROUND

Technical Field

The present disclosure relates to improved systems and methods for purifying and/or concentrating viral vectors. More particularly, the disclosure relates to improved systems and methods using single pass tangential flow filtration to purify and/or concentrate viral vector compositions.

Description of the Related Art

To date, the primary means for purifying biological products such as monoclonal antibodies, therapeutic proteins, vaccines, and other biological products has been through the use of capture chromatography, e.g., affinity chromatography. For viruses, purification processes may also include ultracentrifugation, ion exchange, and affinity and size exclusion chromatography methods. These purification and/or concentration methods are slow, costly, and not easily amenable to large scale viral vector production for use in therapeutic products. Moreover, these methods are limited in their ability to continuously purify and/or concentrate vector being feed from a bioreactor comprising producer cells.

Accordingly, as described further herein, there is a need for improved methods and systems for large scale production of highly pure and concentrated viral vector compositions, particularly for use with continuous vector production systems.

BRIEF SUMMARY

The present disclosure generally relates, in part, to improved methods and systems for purification and concentration of viral vector compositions. Particularly, the invention provides methods of purifying and/or concentrating viral vector compositions comprising single pass tangential flow filtration. More particularly, the methods and systems are useful for large scale production of viral vector compositions (e.g., continuous and/or batch fed production).

In various embodiments, a method of purifying and/or concentrating a viral vector composition comprising the steps of: (a) feeding a composition comprising a viral vector through an SPTFF system, the system comprising: (i) a feed pump; and (ii) an SPTFF filtration module, wherein the SPTFF filtration module purifies the viral vector composition; and (b) collecting a purified viral vector composition. In some embodiments, the viral vector is derived from an adeno-associated virus or a lentivirus. In some embodiments, the viral vector is derived from a lentivirus.

In particular embodiments, the SPTFF system does not comprise an affinity chromatography component.

In various embodiments, the SPTFF system comprises one or more SPTFF filtration modules. In some embodiments, the SPTFF filtration module(s) comprise three or more tangential flow filtration (TFF) cassettes or hollow fiber cartridges. In some embodiments, the SPTFF filtration module(s) comprise four or more tangential flow filtration (TFF) cassettes or hollow fiber cartridges. In some embodiments, the SPTFF filtration module(s) comprise five or more tangential flow filtration (TFF) cassettes or hollow fiber cartridges. In some embodiments, the SPTFF filtration module(s) comprise six or more tangential flow filtration (TFF) cassettes or hollow fiber cartridges. In some embodiments, the SPTFF filtration module(s) comprise seven or more tangential flow filtration (TFF) cassettes or hollow fiber cartridges. In some embodiments, the SPTFF filtration module(s) comprise eight or more, nine or more, ten or more, eleven or more, twelve or more, or thirteen or more, tangential flow filtration (TFF) cassettes or hollow fiber cartridges.

In various embodiments, the TFF cassettes comprise one or more flat sheet membranes. In various embodiments, the hollow fiber cartridges comprise one or more hollow fiber membranes. In some embodiments, the one or more membranes comprise an average molecular weight cut-off (MWCO) selected from the group consisting of: about 1 kDa, about 5 kDa, about 10 kDa, about 20 kDa, about 30 kDa, about 40 kDa, about 50 kDa, about 60 kDa, about 70 kDa, about 80 kDa, about 90 kDa, about 100 kDa, about 200 kDa, about 300 kDa, about 400 kDa, and about 500 kDa. In some embodiments, the one or more membranes comprises an MWCO of about 30 kDa. In some embodiments, the one or more membranes comprises an MWCO of about 300 kDa.

In various embodiments, two or more TFF cassettes or hollow fiber cartridges are configured for processing in parallel. In some embodiments, two or more TFF cassettes or hollow fiber cartridges are configured for processing in serial. In some embodiments, the TFF cassettes or hollow fiber cartridges are configured for processing in parallel and serial.

In various embodiments, the viral vector composition follows a flow path through the SPTFF system and/or SPTFF filtration module.

In various embodiments, the TFF cassettes or hollow fiber cartridges have an effective membrane area. In some embodiments, the effective membrane area decreases along the flow path within the SPTFF filtration module.

In various embodiments, the system comprises (a) a viral vector composition feed flow rate entering the SPTFF filtration module and (b) a viral vector composition retentate flow rate exiting the SPTFF filtration module. In some embodiments, the viral vector composition feed flow rate entering the SPTFF filtration module is at least about 10× greater than the viral vector composition retentate flow rate exiting the SPTFF filtration module. In some embodiments, the viral vector composition retentate flow rate exiting the SPTFF filtration module is at least about 10× less than the viral vector composition feed flow rate entering the SPTFF filtration module.

In various embodiments, the SPTFF filtration module has an average transmembrane pressure (TMP) of about 10 psi or lower, about 9 psi or lower, about 8 psi or lower, about 7 psi or lower, about 6 psi or lower, about 5 psi or lower, about 4 psi or lower, about 3 psi or lower, or about 2 psi or lower. In some embodiments, the SPTFF filtration module has an average transmembrane pressure (TMP) of about 5 psi or lower.

In various embodiments, the feed pump is positioned immediately before the SPTFF filtration module and continuous with the flow path. In some embodiments, the system further comprises a retentate pump after the SPTFF filtration module(s) and continuous with the flow path. In some embodiments, the system further comprises a waste or permeate pump.

In some embodiments, the SPTFF system does not comprise centrifugation.

In various embodiments, the viral vector composition is not recirculated through the SPTFF system, SPTFF filtration module(s), and/or any TFF cassettes or hollow fiber cartridges within the SPTFF filtration module(s).

In various embodiments, the system further comprises a single-pass diafiltration (SPDF) component following the SPTFF filtration module(s).

In various embodiments, the system further comprises a polishing chromatography component after the SPTFF filtration module(s). In some embodiments, the polishing chromatography component comprises a hydrophobic interaction resin, a size exclusion resin, and/or an ion exchange resin. In some embodiments, the polishing chromatography component comprises an anion exchange resin. In some embodiments, the polishing chromatography component removes host cell protein and/or host gDNA from the viral vector composition.

In various embodiments, the SPTFF system further comprises a 0.22 μM final filter.

In various embodiments, the SPTFF system further comprises a mechanism to add a nuclease to the viral vector composition. In some embodiments, the nuclease is added to the viral vector composition prior to feeding the viral vector composition through the SPTFF filtration module. In some embodiments, the nuclease is added to the viral vector composition after the viral vector composition has passed through the SPTFF filtration module. In some embodiments, the nuclease is a denarase DNA endonuclease or the like.

In various embodiments, the system further comprises a bioreactor. In some embodiments, the bioreactor comprises viral vector producer cells. In some embodiments, the viral vector producer cells are lentiviral vector producer cells. In some embodiments, the producer cells are maintained in suspension. In some embodiments, the producer cells are HEK 293 cells. In some embodiments, the HEK 293 cells are HEK 293T or HEK 293F cells.

In various embodiments, the viral vector comprises a polynucleotide encoding a therapeutic protein. In some embodiments, the therapeutic protein is an engineered αβ TCR, an engineered γδ TCR, a dimerizing agent regulated immunoreceptor complex (DARIC), a chimeric antigen receptor (CAR), a chimeric costimulatory receptor (CCR), a bispecific T cell engager (BiTE), a zetakine receptor, a β-globin protein, an ABCD1 polypeptide, an erythropoietin receptor or fragment thereof, an endonuclease, or a megaTAL. In some embodiments, the viral vector comprises a polynucleotide encoding an shRNA, a shmiR, or a guide RNA.

DETAILED DESCRIPTION

A. Overview

Figure 1A:
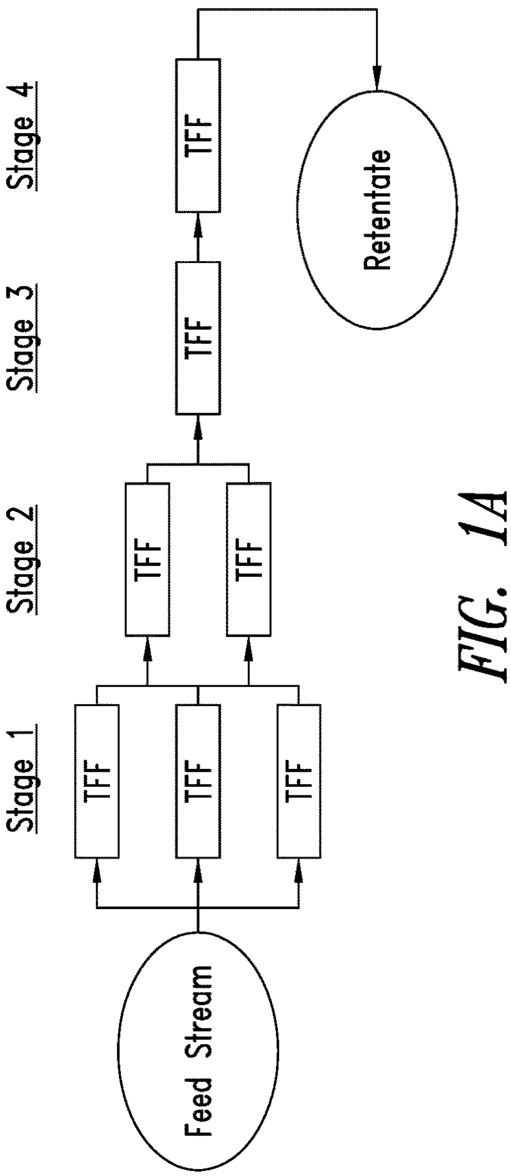
FIGS. 1A and 1B show schematics of a single pass tangential flow filtration (SPTFF) module having similarly sized tangential flow filtration (TFF) cassettes or hollow fiber cartridges configured for processing both in parallel and serially.

The present disclosure generally relates, in part, to improved single pass tangential flow filtration (SPTFF) methods for purifying and concentrating viral vector compositions for use in the manufacturing of drug products. In various embodiments, these methods are particularly suitable for use with large batch (e.g., bulk-fed) or continuous purification/concentration systems, e.g., viral vector produced in bioreactors. In some embodiments, a viral vector is produced using producer cells.

The present inventors have discovered that use of an SPTFF system is surprisingly effective as the primary means for large batch or continuous purification/concentration of viral vector compositions compared to systems using industry standard capture or affinity chromatography. Additionally, the present inventors have discovered that decreasing the transmembrane pressure (TMP) within a SPTFF system surprisingly results in improved purification and concentration of the viral vector composition.

In one aspect, a method for purifying and/or concentrating viral vector is provided. In some embodiments, the method comprises the steps of: (a) feeding a composition comprising a viral vector through an SPTFF system, the system comprising: (i) a feed pump; and (ii) an SPTFF filtration module, wherein the SPTFF filtration module purifies the viral vector composition; and (b) collecting a purified viral vector composition.

In another aspects, an SPTFF system for purifying and/or concentrating viral vector is provided. In some embodiments, a system comprises a feed pump and an SPTFF filtration module, wherein the SPTFF filtration module purifies the viral vector composition.

In particular embodiments, a viral vector is derived from an adeno-associated virus (AAV) or a lentivirus.

In preferred embodiments, the methods or SPTFF systems described herein are used as the primary means for the viral vector purification and concentration in manufacturing processes, particularly in large batch and/or continuous manner operations. In various embodiments, the systems and methods described herein, do not comprise a capture or affinity chromatography component or step. In some embodiments, a viral vector composition is not recirculated through an SPTFF system or SPTFF filtration module. In some embodiments, the methods contemplated herein do not comprise centrifugation.

In various embodiments, an SPTFF filtration module comprises four or more, five or more, six or more, seven or more, eight or more, nine or more, ten or more, eleven or more, twelve or more, or thirteen or more tangential flow filtration (TFF) cassettes. In various embodiments, an SPTFF filtration module comprises four or more, five or more, six or more, seven or more, eight or more, nine or more, ten or more, eleven or more, twelve or more, or thirteen or more hollow fiber TFF cartridges.

In some embodiments, an TFF cassettes or hollow fiber TFF cartridges operate in serial and/or in parallel. Accordingly, in an SPTFF system, the feed (e.g., viral vector composition) can flow over one cassette or cartridge (or groups of cassettes or cartridges) at a time (a.k.a., serial operation), or be split between several cassettes or cartridges (a.k.a., parallel operation). In some embodiments, the feed is split between several cassettes or cartridges in parallel (e.g., in a group or stage), and several groups of cassettes or cartridges are linked serially.

In various embodiments, TFF cassettes and/or hollow fiber TFF cartridges operating in serial and/or in parallel have an effective membrane area. For example, the effective membrane area of a cassette or cartridge operating in serial mode would be equal to the size of the membrane. However, the effective membrane area of several cassettes or cartridges operating in parallel mode would have an effective membrane area equal to the sum of the membrane areas of all cassettes or cartridges at any given step along the flow path (see, e.g., FIGS. 1A and 1B). In particular embodiments, the effective membrane area decreases along the flow path within the SPTFF filtration module.

In various embodiments, the flow rate of a composition (e.g., the feed) entering an SPTFF filtration module is 10× greater than a retentate flow rate exiting the SPTFF filtration module. In some embodiments, a composition retentate flow rate exiting an SPTFF filtration module is 10× less than a feed flow rate entering the SPTFF filtration module.

In various embodiments, an SPTFF filtration module has an average transmembrane pressure (TMP) of about 10 psi or lower, about 9 psi or lower, about 8 psi or lower, about 7 psi or lower, about 6 psi or lower, about 5 psi or lower, about 4 psi or lower, about 3 psi or lower, or about 2 psi or lower. In some embodiments, a system comprises a feed pump, retentate pump, and/or a permeate/waste pump.

In various embodiments, the system further comprises a bioreactor, a single-pass diafiltration (SPDF) component, a polishing chromatography component, and/or a final filter. In some embodiments, a polishing chromatography component comprises a hydrophobic interaction resin, a size exclusion resin, and/or an ion exchange resin. In some embodiments, a polishing chromatography component comprises an anion exchange resin. In some embodiments, a bioreactor comprises producer cells. In some embodiments, the method further comprises the step of adding a nuclease to the composition.

In various embodiments, a viral vector comprises a polynucleotide encoding a therapeutic protein. In various embodiments, a viral vector comprises a polynucleotide encoding an engineered αβ TCR, an engineered γδ TCR, a dimerizing agent regulated immunoreceptor complex (DARIC), a chimeric antigen receptor (CAR), a chimeric costimulatory receptor (CCR), a bispecific T cell engager (BiTE), a zetakine receptor, a chimeric TGFβ receptor (CTBR), a β-globin protein, an ABCD1 polypeptide, an erythropoietin receptor or fragment thereof, an endonuclease, or a megaTAL. In some embodiments, a viral vector comprises a polynucleotide encoding an shRNA, a shmiR, or a guide RNA.

Techniques for recombinant (i.e., engineered) DNA, peptide and oligonucleotide synthesis, immunoassays, tissue culture, transformation (e.g., electroporation, lipofection), enzymatic reactions, purification and related techniques and procedures may be generally performed as described in various general and more specific references in microbiology, molecular biology, biochemistry, molecular genetics, cell biology, virology and immunology as cited and discussed throughout the present specification. See, e.g., Sambrook et al., Molecular Cloning: A Laboratory Manual, 3d ed., Cold Spring Harbor Laboratory Press, Cold Spring Harbor, N.Y.; Current Protocols in Molecular Biology (John Wiley and Sons, updated July 2008); Short Protocols in Molecular Biology: A Compendium of Methods from Current Protocols in Molecular Biology, Greene Pub. Associates and Wiley-Interscience; Glover, DNA Cloning: A Practical Approach, vol. I & II (IRL Press, Oxford Univ. Press USA, 1985); Current Protocols in Immunology (Edited by: John E. Coligan, Ada M. Kruisbeek, David H. Margulies, Ethan M. Shevach, Warren Strober 2001 John Wiley & Sons, NY, NY); Real-Time PCR: Current Technology and Applications, Edited by Julie Logan, Kirstin Edwards and Nick Saunders, 2009, Caister Academic Press, Norfolk, UK; Anand, Techniques for the Analysis of Complex Genomes, (Academic Press, New York, 1992); Guthrie and Fink, Guide to Yeast Genetics and Molecular Biology (Academic Press, New York, 1991); Oligonucleotide Synthesis (N. Gait, Ed., 1984); Nucleic Acid The Hybridization (B. Hames & S. Higgins, Eds., 1985); Transcription and Translation (B. Hames & S. Higgins, Eds., 1984); Animal Cell Culture (R. Freshney, Ed., 1986); Perbal, A Practical Guide to Molecular Cloning (1984); Next-Generation Genome Sequencing (Janitz, 2008 Wiley-VCH); PCR Protocols (Methods in Molecular Biology) (Park, Ed., 3rd Edition, 2010 Humana Press); Immobilized Cells And Enzymes (IRL Press, 1986); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Harlow and Lane, Antibodies, (Cold Spring Harbor Laboratory Press, Cold Spring Harbor, N.Y., 1998); Immunochemical Methods In Cell And Molecular Biology (Mayer and Walker, eds., Academic Press, London, 1987); Handbook Of Experimental Immunology, Volumes I-IV (D. M. Weir and CC Blackwell, eds., 1986); Roitt, Essential Immunology, 6th Edition, (Blackwell Scientific Publications, Oxford, 1988); Current Protocols in Immunology (Q. E. Coligan, A. M. Kruisbeek, D. H. Margulies, E. M. Shevach and W. Strober, eds., 1991); Annual Review of Immunology; as well as monographs in journals such as Advances in Immunology.

B. Definitions

Prior to setting forth this disclosure in more detail, it may be helpful to an understanding thereof to provide definitions of certain terms to be used herein.

Unless defined otherwise, all technical and scientific terms used herein have the same meaning as commonly understood by those of ordinary skill in the art to which the invention belongs. Although any methods and materials similar or equivalent to those described herein can be used in the practice or testing of particular embodiments, preferred embodiments of compositions, methods and materials are described herein. For the purposes of the present disclosure, the following terms are defined below.

The articles “a,” “an,” and “the” are used herein to refer to one or to more than one (i.e., to at least one, or to one or more) of the grammatical object of the article. By way of example, “an element” means one element or one or more elements.

The use of the alternative (e.g., "or") should be understood to mean either one, both, or any combination thereof of the alternatives.

The term "and/or" should be understood to mean either one, or both of the alternatives.

As used herein, the term "about" or "approximately" refers to a quantity, level, value, number, frequency, percentage, dimension, size, amount, weight or length that varies 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

In one embodiment, a range, e.g., 1 to 5, about 1 to 5, or about 1 to about 5, refers to each numerical value encompassed by the range. For example, in one non-limiting and merely illustrative embodiment, the range "1 to 5" is equivalent to the expression 1, 2, 3, 4, 5; or 1.0, 1.5, 2.0, 2.5, 3.0, 3.5, 4.0, 4.5, or 5.0; or 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0.

As used herein, the term "substantially" refers to a quantity, level, value, number, frequency, percentage, dimension, size, amount, weight or length that is 80%, 85%, 90%, 91%, 92%, 93%, 94%, 95%, 96%, 97%, 98%, 99% or higher compared to a reference quantity, level, value, number, frequency, percentage, dimension, size, amount, weight or length. In one embodiment, "substantially the same" refers to a quantity, level, value, number, frequency, percentage, dimension, size, amount, weight or length that produces an effect, e.g., a physiological effect, that is approximately the same as a reference quantity, level, value, number, frequency, percentage, dimension, size, amount, weight or length.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are present that materially affect the activity or action of the listed elements.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment. Thus, the appearances of the foregoing phrases in various places throughout this specification are not necessarily all referring to the same embodiment. Furthermore, the particular features, structures, or characteristics may be combined in any suitable manner in one or more embodiments. It is also understood that the positive recitation of a feature in one embodiment, serves as a basis for excluding the feature in a particular embodiment.

The term "SPTFF filtration module" refer to a component in an SPTFF system comprising one or more TFF cassettes or hollow fiber TFF cartridges. The SPTFF filtration module may also comprise a "holder" for the TFF cassettes. The SPTFF filtration module may also comprise one or more manifolds or manifold segments configured to carry a feed, retentate, permeate, and/or waste to and from the TFF cassettes and/or hollow fiber TFF cartridges.

The term "manifold segment" refers to a block having a plurality of manifolds, including a manifold for carrying a feed, a manifold for carrying a retentate and a manifold for carrying a permeate.

A "TFF cassette" or "cassette" refers to a plate-and-frame structure comprising a filtration membrane (e.g., an ultrafiltration membrane, a microfiltration membrane) and separate feed/retentate and permeate flow channels suitable for SPTFF processes.

The term "hollow fiber TFF cartridge," "hollow fiber cartridge" or "cartridge" refers to a structure (e.g., a tube-like structure) comprising channels formed by a bundle of hollow fibers (membranes). Such cartridges typically comprise capped ends, wherein the cartridge comprises an inlet for a feed sample or solution (e.g., a viral vector composition), and one or more separate outlets for the retentate and permeate.

The term "hollow fiber membrane" refers to a class of artificial filtration membranes containing a semi-permeable barrier in the form of a hollow fiber.

The term "filtration membrane" refers to a selectively permeable membrane for separating a feed into a permeate stream and a retentate stream using an SPTFF process.

Filtration membranes include, but are not limited to, ultrafiltration (UF) membranes, microfiltration (MF) membranes, reverse osmosis (RO) membranes and nanofiltration (NF) membranes. The filtration membrane may be a flat sheet or hollow fiber.

The terms "microfiltration membranes" and "MF membranes" refer to membranes that have pore sizes in the range between about 0.1 micrometers to about 10 micrometers.

The terms "ultrafiltration membrane" and "UF membrane" refer to a membrane that has pore sizes in the range of between about 10 nanometer to about 100 nanometers (i.e., about 0.01 micrometers to about 0.1 micrometers).

The terms "nanofiltration membrane" and "NF membrane" refer to membranes that have pore sizes in the range between about 1 nanometers to about 10 nanometers (i.e., about 0.001 micrometers to about 0.01 micrometers).

Additional definitions are set forth throughout this disclosure.

C. Single Pass Tangential Flow Filtration (SPTFF) Systems

Tangential flow filtration (TFF) is a process that uses membranes to separate components in a liquid solution or suspension (e.g., a feed sample) on the basis of size, molecular weight or other differences. In these processes, the feed sample is pumped tangentially along the membrane surface and particles or molecules which are too large to pass through the membrane are retained and returned to a process tank for additional passes across the membrane (i.e., recirculation) until the feed sample is sufficiently clarified, concentrated, or purified. The cross-flow nature of TFF minimizes membrane fouling, thus permitting high volume processing per batch.

Traditional batch-fed recirculation TFF processes, however, are limited due to the size and minimum working volume of existing TFF systems. Single-Pass TFF (SPTFF) allows direct flow-through concentration of a product (e.g., protein) in the absence of recirculation, which reduces overall system size through elimination of mechanical components and permits continuous operation at high conversion levels. However, use of such SPTFF systems as the primary means for viral vector purification/concentration in biomanufacturing has not been fully realized.

Without wishing to be bound by any particular theory, it is contemplated that SPTFF systems have not been used as the primary means to purify/concentrate viral particles in large scale biomanufacturing systems (e.g., large batch-fed or continuous viral vector production systems) because of the inherent difficulties in assembling SPTFF systems that can effectively purify/concentrate viral vectors to the high standards required for drug manufacturing. Moreover, it is difficult to create producer cells that can continually produce viral vectors for more than a few days (let alone weeks), which would enable the use of continuously- or large batch-fed SPTFF systems for purification/concentration of the viral vector. The present inventors have developed SPTFF systems and methods that are surprisingly effective for purifying/concentrating viral vectors (e.g., in a continuous- or large batch-fed manner), thus reducing costs, processing time, and product yield and recovery in viral vector manufacturing.

In various embodiments, improved systems and methods for purifying and/or concentrating viral vector compositions using single pass tangential flow filtration (SPTFF) are provided. In particular embodiments, systems and methods contemplated herein are useful for the manufacturing of viral vector compositions in a continuous or large batch-fed manner.

As used herein the term "SPTFF system" refers to a single pass tangential flow filtration (SPTFF) system that is configured for operation in a single-pass mode, i.e., wherein a feed sample (e.g., a viral vector composition) passes only once through the system, and is not recirculated through the system or SPTFF filtration module(s). In some embodiments, a feed sample (e.g., viral vector composition) is not recirculated through an SPTFF filtration module used for purification and/or concentration, but is recirculated through one or more TFF filtration modules used for other purposes, e.g., diafiltration. In some embodiments, a feed sample (e.g., viral vector composition) is not recirculated through any TFF filtration module within an SPTFF system.

In various embodiments, an SPTFF system, and related methods, for purifying and/or concentrating viral vector is provided. In some embodiments, a method comprises the steps of: (a) feeding a composition comprising viral vector through an SPTFF system, the system comprising: (i) a feed pump; and (ii) an SPTFF filtration module, wherein the SPTFF filtration module purifies the viral vector composition; and (b) collecting a purified viral vector composition. In particular embodiments, a viral vector is derived from an adeno-associated virus (AAV) or lentivirus. In some embodiments, the viral vector is an anellovector.

In various embodiments, systems and methods contemplated herein do not comprise an affinity or capture chromatography component or step. In preferred embodiments, a viral vector composition is not recirculated through an SPTFF system or the SPTFF filtration module. In some embodiments, the method or system does not comprise centrifugation.

In various embodiments, an SPTFF system or related method may comprise different components (e.g., units and/or modules) to assist in processing. In general, SPTFF systems useful for performing the methods contemplated herein can be assembled and operated using standard, existing TFF system components. Examples of TFF system components that are commercially available include, without limitation, one or more bioreactor(s), holding tank(s) or vessel(s), waste tank(s) or vessel(s), feed line(s), SPTFF filtration module(s), TFF cassette(s) comprising filtration membrane(s), cassette holder(s), hollow fiber cartridge(s), chromatography component(s), diafiltration component(s), ultrafiltration membrane(s)/filter(s), microfiltration membrane(s)/filter(s), conduits (e.g., tubing, piping) for feed, retentate and permeate, a housing or enclosure, valve(s), gasket(s), pump module(s) (e.g., pump module comprising a pump housing, diaphragm and check valve), sampling port (s), T-line(s) (e.g., for in-line buffer addition), valve sensor (s), flow meters(s), one or more reservoirs (e.g., bioprocess containers), pressure gauge(s), and vial filling component(s) (see, e.g., FIG. 3 and FIG. 4).

In various embodiments, one or more of the components are fluidly connected to effectuate continuous flow of the feed sample (e.g., viral vector composition) between components. The phrase "fluidly connected" refers to two or more components of an SPTFF system (e.g., two or more manifolds, two or more manifold segments, two or more TFF cassettes, two or more hollow fiber TFF cartridges, or any combination thereof), that are connected by one or more conduits (e.g., a feed channel, a retentate channel, a permeate channel) such that a feed sample can flow from one component to the other.

The term "processing" refers to the act of filtering (e.g., by SPTFF) a feed stream containing a viral vector composition and subsequently recovering the viral vector in a concentrated and/or purified form. The concentrated viral vector can be recovered from the filtration system (e.g., an SPTFF system) in either a retentate stream or permeate stream depending on the size of the viral vector and the pore size of the filtration membrane. In preferred embodiments, the viral vector is recovered from the filtration system in the retentate stream.

The terms "purification", "purify", "purified", and "purifying", refer to a procedure that enriches the amount of one or more components of interest (e.g., viral vectors) relative to one or more other components of a sample (e.g., host cell protein). For example, in particular embodiments, the SPTFF systems contemplated herein removes host cell protein (HCP) from the composition—thereby reducing host cell protein concentration—while enriching for viral vectors. As used herein, the terms "purification", "purify", "purified", and "purifying" do not mean removing all material other than the component of interest from the sample.

The terms "feed," "feed sample" and "feed stream" refer to the solution (e.g., viral vector composition) that is delivered to an SPTFF filtration module to be filtered. The feed that is delivered to an SPTFF filtration module for filtration can be, for example, feed from a feed container (e.g., vessel, tank, or bioreactor) external to or integrated within the SPTFF system.

The term "filtration" generally refers to the act of separating a feed sample into two streams, a permeate and a retentate, using membranes.

The terms "permeate" and "filtrate" refer to that portion of a feed that has permeated through a membrane.

The term "retentate" refers to the portion of a feed that has been retained by a membrane, and a retentate is the stream enriched in a retained species.

The term "feed line" or "feed channel" refers to a conduit for conveying a feed from a feed source (e.g., a feed container, vessel, tank, or bioreactor) to one or more processing components in a filtration assembly (e.g., an SPTFF system or SPTFF filtration module).

The term "retentate line" or "retentate channel" refers to a conduit in a filtration assembly for carrying retentate.

The term "permeate line" or "permeate channel" refers to a conduit in a filtration assembly for carrying permeate.

In various embodiments, SPTFF systems and related methods contemplated herein are useful for obtaining a purified and/or concentrated viral vector compositions suitable for in vitro and/or in vivo applications. In particular embodiments, purified and/or concentrated viral vector compositions are suitable for in vivo administration and/or manufacturing of gene therapy products, including but not limited to cellular gene therapy products and vaccines. In preferred embodiments, purified and/or concentrated viral vector compositions are suitable for manufacturing of cellular therapies. In further preferred embodiments, purified and/or concentrated viral vector compositions are useful for gene therapy in vitro, ex vivo, or in vivo.

In various embodiments, SPTFF systems and related methods provided herein comprise one or more SPTFF filtration modules or components that are fluidly connected. In some embodiments, an SPTFF system and related methods comprise a feed inlet on a first SPTFF filtration module and a retentate outlet on a last SPTFF filtration module. In some embodiments, the first and last SPTFF filtration module are the same module, i.e., the system comprises only one SPTFF filtration module.

In various embodiments, SPTFF systems and related methods comprise one or more flow paths. The expression "flow path" refers to a channel supporting the flow of a solution (e.g., feed, retentate, permeate, or composition) through all or part of an SPTFF system. Thus, an SPTFF system can have multiple flow paths, including a flow path through an entire system from a feed inlet to a retentate outlet, a flow path within an SPTFF filtration module (e.g., a flow path through TFF cassettes), a flow path between two or more adjacent SPTFF filtration modules (e.g., a flow path between manifold segments in adjacent SPTFF filtration modules), and a flow path between two or more adjacent TFF cassettes or hollow fiber cartridges (e.g., a flow path between manifold segments in adjacent SPTFF filtration modules). The flow path can have any topology which supports tangential flow (e.g., straight, coiled, arranged in zigzag fashion). The flow path can be parallel or serial. Furthermore, the flow path can be open, as in an example of channels formed by hollow fiber membranes, or have one or more flow obstructions, for example, of rectangular channels formed by flat-sheet membranes spaced apart by woven or non-woven spacers, or gaskets (e.g., silicone gaskets).

In some embodiments, SPTFF systems and related methods comprise one or more bioreactors. For example, SPTFF systems and related methods comprise one, two, three, four, or five, bioreactors.

The term "bioreactor" as used herein, refers to any manufactured or engineered device or system that supports a biologically active environment. In some instances, a bioreactor is a vessel in which a cell culture process is carried out. Such a process may either be aerobic or anaerobic. Commonly used bioreactors are typically cylindrical, ranging in size from liters to cubic meters, and are often made of stainless steel. In some embodiments described herein, a bioreactor is made of a material other than steel and is disposable or single-use. It is contemplated that the total volume of a bioreactor may be any volume ranging from 100 mL to up to 10,000 Liters or more, depending on a particular process. In some embodiments according to the processes and systems described herein, the bioreactor is connected to a unit operation such as a depth filter. In some embodiments described herein, a bioreactor is used for both cell culturing as well as for precipitation, where a precipitant may be added directly to a bioreactor to precipitate one or more impurities.

In some embodiments, a bioreactor is fluidly connected to one or more components within an SPTFF system. For example, in some embodiments, a bioreactor is fluidly connected to an SPTFF filtration module. In some embodiments, a bioreactor is fluidly connected to a holding tank or vessel, which may also be fluidly connected to an SPTFF filtration module (e.g., via a feed inlet).

A bioreactor can be any type of bioreactor like a batch or a fed batch bioreactor or a continuous bioreactor like a continuous perfusion fermentation bioreactor. A bioreactor can be made of any suitable material and can be of any size. Typical materials are stainless steel or plastic. In a preferred embodiment, a bioreactor is a disposable bioreactor, e.g., in form of a flexible, collapsible bag, designed for single-use. Cells growing in bioreactors may be submerged in liquid medium or may be attached to the surface of a solid medium. Submerged cultures may be suspended or immobilized. In some embodiments, a bioreactor is fluidly connected to the SPTFF system. In some embodiments, a bioreactor is fluidly connected to a holding tank (e.g., an intermediate holding tank).

In some embodiments, a bioreactor comprises producer cells. As used herein, the terms "producer cells" or "producer cell line" refers to a cell or cell line which is capable of producing recombinant retroviral particles, comprising a packaging cell line and a transfer vector construct comprising a packaging signal. The production of infectious viral particles and viral stock solutions may be carried out using conventional techniques. Methods of preparing viral stock solutions are known in the art and are illustrated by, e.g., Y. Soneoka et al. (1995) *Nucl. Acids Res.* 23:628-633, and N. R. Landau et al. (1992) *J. Virol.* 66:5110-5113. Infectious virus particles may be collected from the producer cells using conventional techniques. For example, the infectious particles can be collected by cell lysis, or collection of the supernatant of the cell culture, as is known in the art. Optionally, the collected virus particles may be purified if desired. Suitable purification techniques are well known to those skilled in the art.

In some embodiments, producer cells are maintained in suspension within the bioreactor. In some embodiments, producer cells are AAV vector producer cells, anellovector producer cells, or lentiviral vector producer cells. In particular embodiments, the producer cells are lentiviral vector producer cells. In some embodiments, producer cells are HEK 293 cells. In some embodiments, the HEK 293 cells are HEK 293T or HEK 293F cells. In some embodiments, a viral vector comprises a polynucleotide encoding a therapeutic transgene or therapeutic protein.

In various embodiments, the first component in an SPTFF system or method is a bioreactor containing the starting material, e.g., culturing cells expressing a protein or viral vector to be purified.

In various embodiments, SPTFF systems useful for performing the methods contemplated herein further comprise one or more pumps. In some embodiments, the pump is a feed pump. In some embodiments, an SPTFF system comprises one or more feed pumps. In some embodiments, the feed pump is positioned before the SPTFF filtration module(s) within the flow path. In some embodiments, an SPTFF system or method comprises one or more retentate pumps. In some embodiments, the retentate pump is positioned after the SPTFF filtration module(s) within the flow path.

In various embodiments, a retentate pump has a slower flow rate than a feed pump. In some embodiments, an SPTFF system comprises one or more waste or permeate pumps. In some embodiments, waste or permeate pumps have a slower flow rate than feed and/or retentate pumps. In some embodiments, a feed flow rate entering an SPTFF filtration module is at least 7× greater than a retentate flow rate exiting the SPTFF filtration module. In some embodiments, a feed flow rate entering an SPTFF filtration module is at least 8× greater than a retentate flow rate exiting the SPTFF filtration module. In some embodiments, a feed flow rate entering an SPTFF filtration module is at least 9× greater than a retentate flow rate exiting the SPTFF filtration module. In some embodiments, a feed flow rate entering an SPTFF filtration module is at least 10× greater than a retentate flow rate exiting the SPTFF filtration module. In some embodiments, a feed flow rate entering an SPTFF filtration module is at least 11× greater than a retentate flow rate exiting the SPTFF filtration module. In some embodiments, a feed flow rate entering an SPTFF filtration module is at least 12× greater than a retentate flow rate exiting the SPTFF filtration module. In some embodiments, a feed flow rate entering an SPTFF filtration module is at least 7× to 12× greater than a retentate flow rate exiting the SPTFF filtration module.

In some embodiments, a composition retentate flow rate exiting an SPTFF filtration module is at least 7× less than a feed flow rate entering the SPTFF filtration module. In some embodiments, a composition retentate flow rate exiting an SPTFF filtration module is at least 8× less than a feed flow rate entering the SPTFF filtration module. In some embodiments, a composition retentate flow rate exiting an SPTFF filtration module is at least 9× less than a feed flow rate entering the SPTFF filtration module. In some embodiments, a composition retentate flow rate exiting an SPTFF filtration module is at least 10× less than a feed flow rate entering the SPTFF filtration module. In some embodiments, a composition retentate flow rate exiting an SPTFF filtration module is at least 11× less than a feed flow rate entering the SPTFF filtration module. In some embodiments, a composition retentate flow rate exiting an SPTFF filtration module is at least 12× less than a feed flow rate entering the SPTFF filtration module. In some embodiments, a composition retentate flow rate exiting an SPTFF filtration module is at least 7× to 12× less than a feed flow rate entering the SPTFF filtration module.

The present inventors also surprisingly discovered that a lower flow rate, and thus a lower transmembrane pressure, than suggested by certain third party providers/venders of TFF systems (including SPTFF systems), provided increased volumetric and product concentration factors for viral vector compositions. The required flow rate to yield a particular transmembrane pressure is the result of many factors including the total membrane area, membrane type, pore size, membrane flux, total length of the flow path, presence of additional pumps on the retentate and/or permeate lines, line clamps, etc. Accordingly, in some embodiments a feed pump has a flow rate of about 75 ml/min or less, about 100 ml/min or less, about 150 ml/min or less, about 200 ml/min or less, about 250 ml/min or less, about 300 ml/min or less, about 350 ml/min or less, about 400 ml/min or less, about 450 ml/min or less, or about 500 ml/min or less. In some embodiments a feed pump has a flow rate of about 75 ml/min to about 100 ml/min, about 75 ml/min to about 150 ml/min, about 75 ml/min to about 200 ml/min, about 75 ml/min to about 250 ml/min, about 75 ml/min to about 300 ml/min, about 75 ml/min to about 350 ml/min, about 75 ml/min to about 400 ml/min, about 75 ml/min to about 450 ml/min, or about 75 ml/min to about 500 ml/min. In some embodiments a feed pump has a flow rate of about 50 ml/min to about 100 ml/min, about 50 ml/min to about 150 ml/min, about 50 ml/min to about 200 ml/min, about 50 ml/min to about 250 ml/min, about 50 ml/min to about 300 ml/min, about 50 ml/min to about 350 ml/min, about 50 ml/min to about 400 ml/min, about 50 ml/min to about 450 ml/min, or about 50 ml/min to about 500 ml/min. In some embodiments a feed pump has a flow rate of about 25 ml/min to about 100 ml/min, about 25 ml/min to about 150 ml/min, about 25 ml/min to about 200 ml/min, about 25 ml/min to about 250 ml/min, about 25 ml/min to about 300 ml/min, about 25 ml/min to about 350 ml/min, about 25 ml/min to about 400 ml/min, about 25 ml/min to about 450 ml/min, or about 25 ml/min to about 500 ml/min.

In some embodiments, an SPTFF system and related methods comprises a clamp on the permeate line to decrease transmembrane pressure. In some embodiments, the clamp is a partial clamp. In some embodiments, the SPTFF system and related methods comprises a clamp on the retentate line to increase the transmembrane pressure. In some embodiments, the clamp is a partial clamp. A partial clamp allows a reduced volume of retentate or permeate to flow through the clamped line.

In some embodiments, the feed stream flow (e.g., viral vector composition) across the membrane is not stopped to allow it to permeate or to diffuse backwards through the membrane by osmosis.

In various embodiments, SPTFF systems and related methods contemplated herein further comprise a holding tank or vessel. Holding tanks or vessels may be positioned in any position within the system where feed sample (e.g., viral vector composition) is to be retained prior to being fed into another component of the system. For example, a system may comprise an intermediate holding tank designed to hold a viral vector composition prior to being fed into an SPTFF filtration module. Holding tanks or vessels may also be used to hold other components including, but not limited to, medias, buffers, and/or additives.

In various embodiments, SPTFF systems useful for performing the methods contemplated herein further comprise a mechanism to add a nuclease and/or buffer to a viral vector composition. In some embodiments, the nuclease and/or buffer are held in a holding tank or vessel. In some embodiments, the nuclease and/or buffer is added to the viral vector composition in an intermediate holding tank (see, e.g., FIGS. 3 and 4). In some embodiments, Trehalose or a poloxamer is added to the viral vector composition in the intermediate holding tank. In some embodiments, the poloxamer is poloxamer 188. In some embodiments, the intermediate holding tank is positioned before an SPTFF filtration module. In some embodiments, the nuclease/buffer holding tank is fluidly connected to the intermediate holding tank. In some embodiments, the SPTFF system comprises a filter (e.g., ultrafiltration membrane or microfiltration membrane)

fluidly connected to the intermediate holding tank. In some embodiments, the filter is fluidly connected to and between the nuclease/buffer holding tank and the intermediate holding tank. In various embodiments, the nuclease is an endonuclease. In some embodiments, the nuclease is derived from *Serratia marcescens*. In preferred embodiments, the nuclease is a Denerase®.

In various embodiments, SPTFF systems useful for performing the methods contemplated herein further comprise a diafiltration component(s). In some embodiments, the diafiltration component is a single pass diafiltration (SPDF) component. In some embodiments, a diafiltration buffer (e.g., formulation buffer) is held in a tank or vessel which is fluidly connected to the diafiltration component. In some embodiments, the diafiltration component is positioned after an SPTFF filtration module. In some embodiments, the diafiltration component comprises a TFF cassette or hollow fiber cartridge.

In various embodiments, SPTFF systems useful for performing the methods contemplated herein further comprise a chromatography component. In preferred embodiments, the chromatography component is a polishing chromatography component and/or step. The term "polishing chromatography" as used herein refers to SPTFF system components, and related methods, which use chromatography to remove any remaining impurities or aggregates in a viral vector composition after the composition has passed through other purification/filtration steps (e.g., any SPTFF filtration modules/steps).

In some embodiments, the polishing chromatography component and/or method step comprises flow-through chromatography. The term "flow-through chromatography" as used herein refers a chromatography component, or related method step, for purifying or concentrating a product wherein a solution flows over a column which binds impurities while the desired product/molecule/vector does not substantially bind the column (i.e., flows through the column). In some embodiments, a flow-through or polishing chromatography comprises one or more separation mechanisms to bind and remove impurities, including, but not limited to, ion exchange chromatography, size exclusion chromatography, or hydrophobic interaction chromatography, or a combination thereof.

In some embodiments, SPTFF systems and related methods comprise more than one polishing chromatography step. In some embodiments, SPTFF systems and related methods comprise two or more polishing chromatography steps. In some embodiments, SPTFF systems and related methods comprise three or more polishing chromatography steps. In some embodiments, SPTFF systems and related methods comprise one, two, or three polishing chromatography steps.

In various embodiments, SPTFF systems and related methods do not comprise a capture or affinity chromatography step or component as the primary purifying and/or concentrating step or component. In typical purification/concentration systems, the primary purifying/concentrating step is the first filtration step within a purification/concentration system or method. Accordingly, in some embodiments, the SPTFF systems and related methods do not comprise a capture or affinity chromatography step or component as the first filtration step or component. In some embodiments, the SPTFF systems and related methods do not comprise a capture or affinity chromatography step or component.

As used herein, the terms "capture chromatography" or "affinity chromatography" refer to a chromatography component, or related method step, which involves binding and eluting of a desired product (e.g., viral particle) to and from a column. Capture or affinity chromatography typically uses selective non-covalent interactions between an analyte and specific molecule(s) (e.g., a specific ligand coupled to a chromatographic medium). For example, capture or affinity chromatography may use protein G, an antibody, a specific substrate, ligand or antigen as the capture reagent.

In various embodiments, SPTFF systems and related methods contemplated herein comprise additional filters. In some embodiments, the filter is a final filter (i.e., the last filter in the system or method). In some embodiments, the filter is a sterilization filter. In some embodiments, the filter comprises a microfiltration membrane. In some embodiments, the filter comprises an ultrafiltration membrane. In some embodiments, the filter comprises a nanofiltration membrane. In some embodiments, the filter is a 0.22 μm filter.

In various embodiments, SPTFF systems and related methods contemplated herein comprise a vial filling component and/or method step.

D. SPTFF Filtration Modules

In various embodiments, SPTFF systems and related methods comprise one or more SPTFF filtration modules. In some embodiments, the SPTFF filtration module comprises TFF cassettes and/or hollow fiber cartridges. In some embodiments, the cassettes and/or cartridges are configured for processing 1) in parallel, 2) in series, or 3) both in parallel and in series (e.g., using valves, gaskets, diverter plates, manifolds, manifold segments, or and/or conduits).

The expressions "parallel processing", "processing in parallel", "parallel operation", "operate in parallel", "operating in parallel", "operation in parallel", "assembled in parallel", "configured for processing in parallel", and "parallel configuration" refer to distributing a feed sample (e.g., a viral vector composition) in an SPTFF system to two or more filtration components (e.g., SPTFF filtration modules, TFF cassettes, hollow fiber cartridges) in the assembly concurrently for subsequent tangential flow filtration.

The expressions "serial processing", "processing in series", "serial operation" "operate in serial", and "operating in serial", "operation in series", "assembled in series", "configured for processing in series", and "serial configuration" refer to distributing a feed sample (e.g., a viral vector composition) in an SPTFF system to one filtration component (e.g., SPTFF filtration module, TFF cassette, hollow fiber cartridge) at a time, such that the retentate flow of a preceding component serves as the feed flow for a subsequent, adjacent component.

In some embodiments, the feed is split between several cassettes or cartridges in parallel (e.g., in a group or stage), and several groups of cassettes or cartridges are linked serially.

Preferably, cassettes or cartridges that are configured for processing in parallel precede the cassettes or cartridges that are configured for processing in series. In particular embodiments, all of the SPTFF filtration modules in an SPTFF system have cassettes that are configured for processing in parallel (e.g., one or more groups or stages of cassettes or cartridges configured in parallel and linked serially), except for the last two cassettes or cartridges, which are configured for processing in series (see, e.g., FIGS. 1A and 1B). In some embodiments, all of the SPTFF filtration modules in an SPTFF system have cassettes that are configured for processing in parallel (e.g., one or more groups or stages of cassettes or cartridges configured in parallel and linked serially), except for the last cassette or cartridge, which is configured for processing in series. In preferred embodiments, the effective membrane area decreases along the flow path through the SPTFF filtration module.

The term "effective membrane area" refers to the total area of the TFF membrane(s) at any given stage/point along the flow path within an SPTFF filtration module. For example, if the SPTFF filtration module comprises TFF cassettes or hollow fiber cartridges are configured for processing in parallel (see, e.g., stages 1-2 in FIG. 1A, and stages 1~4 in FIG. 1B), then the effective membrane area is the sum of the membrane areas of all the cassettes or cartridges at any given stage or step along the flow path.

Figure 1B:
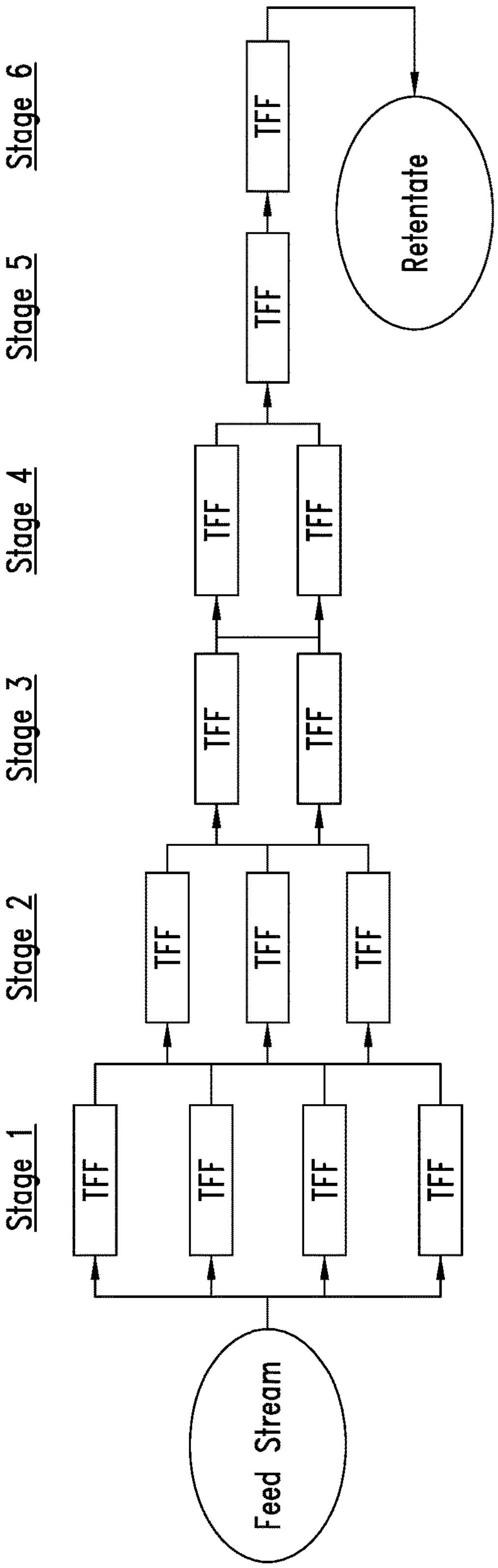

As shown in FIG. 1A, the SPTFF filtration module has a flow path comprising 4 stages. At the first stage, the composition flows through three TFF cassettes or hollow fiber cartridges configured for processing in parallel. Thus, the effective membrane area at stage 1 is the sum of the membrane areas of all three TFF cassettes or hollow fiber cartridges. At the second stage, the composition flows through two TFF cassettes or hollow fiber cartridges configured for processing in parallel. The effective membrane area at stage 2 is the sum of the membrane areas of two TFF cassettes or hollow fiber cartridges. At the third and fourth stages, the composition flows through two single TFF cassettes or hollow fiber cartridges configured for processing serially. The effective membrane area at each of stages 3 and 4 equals the membrane area of each TFF cassette or hollow fiber cartridge. Accordingly, as shown in FIGS. 1A and 1B, the effective membrane area generally decreases along the flow path of the feed sample (e.g., viral vector composition) within an SPTFF filtration module.

Figure 2A:
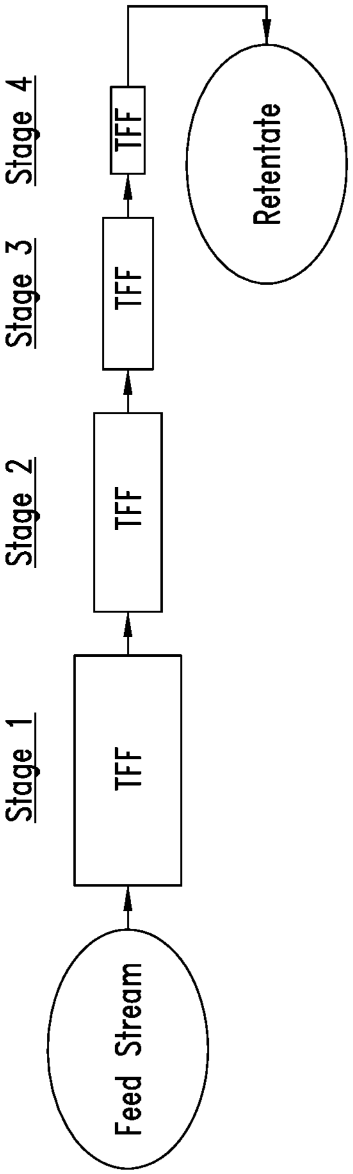
FIGS. 2A and 2B show schematics of an SPTFF module having TFF cassettes or hollow fiber cartridges configured for processing serially and decreasing in effective membrane area along the flow path.
Figure 2B:
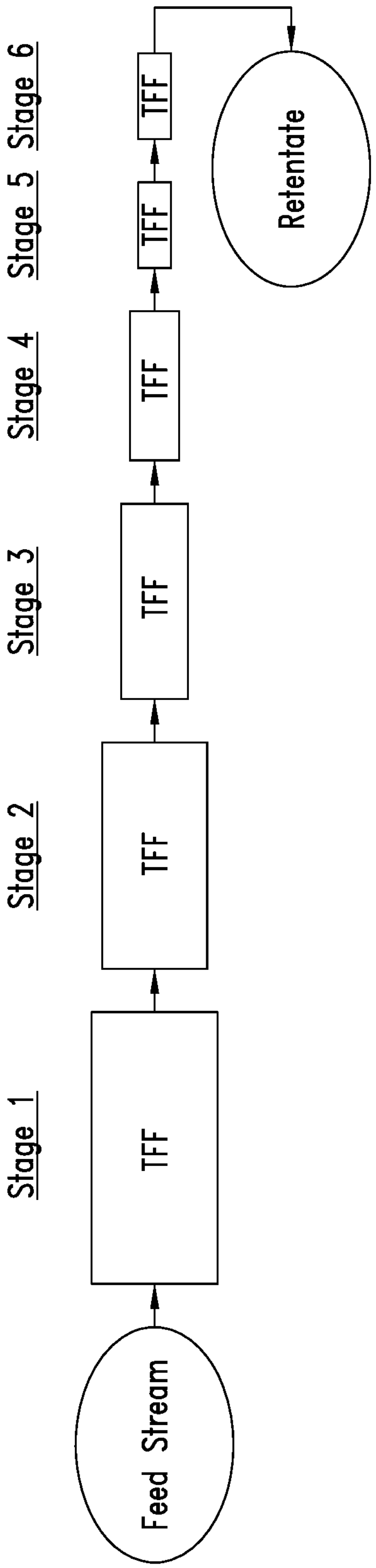

Alternatively, one or more TFF cassettes or hollow fiber cartridges may have different effective membrane areas and be assembled in decreasing order. For example, as shown in FIGS. 2A and 2B, the TFF cassettes or hollow fiber cartridges are configured for processing in serial and in decreasing order of effective membrane area at each stage. In some embodiments, an SPTFF filtration module may comprise aspects of both systems shown in FIGS. 1A-1B and FIGS. 2A-2B. For example, in some embodiments, the SPTFF filtration module comprises both TFF cassettes or hollow fiber cartridges having different effective membrane sizes and parallel assemble. In some embodiments, the SPTFF filtration module comprises TFF cassettes or hollow fiber cartridges having different effective membrane sizes and assembled in parallel and in serial.

In various embodiments, depending on the configuration (i.e., a parallel or serial configuration) one or more TFF cassettes and/or hollow fiber cartridges comprise an effective membrane area of about 0.01 $m^2$, about 0.015 $m^2$, about 0.02 $m^2$, about 0.025 $m^2$, about 0.03 $m^2$, about 0.035 $m^2$, about 0.04 $m^2$, about 0.045 $m^2$, about 0.05 $m^2$, about 0.055 $m^2$, about 0.06 $m^2$, about 0.065 $m^2$, about 0.07 $m^2$, about 0.075 $m^2$, about 0.08 $m^2$, about 0.085 $m^2$, about 0.09 $m^2$, about 0.095 $m^2$, about 0.1 $m^2$, about 0.11 $m^2$, about 0.12 $m^2$, about 0.13 $m^2$, about 0.14 $m^2$, about 0.15 $m^2$, about 0.16 $m^2$, about 0.17 $m^2$, about 0.18 $m^2$, about 0.19 $m^2$, about 0.20 $m^2$, about 0.21 $m^2$, about 0.22 $m^2$, about 0.23 $m^2$, about 0.24 $m^2$, about 0.25 $m^2$, about 0.26 $m^2$, about 0.27 $m^2$, about 0.28 $m^2$, about 0.29 $m^2$, about 0.30 $m^2$, about 0.31 $m^2$, about 0.32 $m^2$, about 0.33 $m^2$, about 0.34 $m^2$, about 0.35 $m^2$, about 0.40 $m^2$, about 0.45 $m^2$, about 0.50 $m^2$, about 0.55 $m^2$, about 0.60 $m^2$, about 0.65 $m^2$, about 0.70 $m^2$, about 0.75 $m^2$, about 0.80 $m^2$, about 0.85 $m^2$, about 0.90 $m^2$, about 0.95 $m^2$, about 1.0 $m^2$, about 1.1 $m^2$, about 1.2 $m^2$, about 1.3 $m^2$, about 1.4 $m^2$, about 1.5 $m^2$, about 1.6 $m^2$, about 1.7 $m^2$, about 1.8 $m^2$, about 1.9 $m^2$, about 2.0 $m^2$, about 2.1 $m^2$, about 2.2 $m^2$, about 2.3 $m^2$, about 2.4 $m^2$, about 2.5 $m^2$, about 3.0 $m^2$, about 3.5 $m^2$, about 4.0 $m^2$, about 4.5 $m^2$, about 5.0 $m^2$, about 6.0 $m^2$, about 6.5 $m^2$, about 7.0 $m^2$, about 7.5 $m^2$, about 8.0 $m^2$, about 8.5 $m^2$, about 9.0 $m^2$, about 9.5 $m^2$, about or 10 $m^2$.

In various embodiments, depending on the configuration (i.e., a parallel or serial configuration) one or more TFF cassettes and/or hollow fiber cartridges comprise an effective membrane area of about 0.01 $m^2$ to about 10 $m^2$, about 0.015 $m^2$ to about 10 $m^2$, about 0.02 $m^2$ to about 10 $m^2$, about 0.025 $m^2$ to about 10 $m^2$, about 0.03 $m^2$ to about 10 $m^2$, about 0.035 $m^2$ to about 10 $m^2$, about 0.04 $m^2$ to about 10 $m^2$, about 0.045 $m^2$ to about 10 $m^2$, about 0.05 $m^2$ to about 10 $m^2$, about 0.055 $m^2$ to about 10 $m^2$, about 0.06 $m^2$ to about 10 $m^2$, about 0.065 $m^2$ to about 10 $m^2$, about 0.07 $m^2$ to about 10 $m^2$, about 0.075 $m^2$ to about 10 $m^2$, about 0.08 $m^2$ to about 10 $m^2$, about 0.085 $m^2$ to about 10 $m^2$, about 0.09 $m^2$ to about 10 $m^2$, about 0.095 $m^2$ to about 10 $m^2$, about 0.1 $m^2$ to about 10 $m^2$, about 0.11 $m^2$ to about 10 $m^2$, about 0.12 $m^2$ to about 10 $m^2$, about 0.13 $m^2$ to about 10 $m^2$, about 0.14 $m^2$ to about 10 $m^2$, about 0.15 $m^2$ to about 10 $m^2$, about 0.16 $m^2$ to about 10 $m^2$, about 0.17 $m^2$ to about 10 $m^2$, about 0.18 $m^2$ to about 10 $m^2$, about 0.19 $m^2$ to about 10 $m^2$, about 0.20 $m^2$ to about 10 $m^2$, about 0.21 $m^2$ to about 10 $m^2$, about 0.22 $m^2$ to about 10 $m^2$, about 0.23 $m^2$ to about 10 $m^2$, about 0.24 $m^2$ to about 10 $m^2$, about 0.25 $m^2$ to about 10 $m^2$, about 0.26 $m^2$ to about 10 $m^2$, about 0.27 $m^2$ to about 10 $m^2$, about 0.28 $m^2$ to about 10 $m^2$, about 0.29 $m^2$ to about 10 $m^2$, about 0.30 $m^2$ to about 10 $m^2$, about 0.31 $m^2$ to about 10 $m^2$, about 0.32 $m^2$ to about 10 $m^2$, about 0.33 $m^2$ to about 10 $m^2$, about 0.34 $m^2$ to about 10 $m^2$, about 0.35 $m^2$ to about 10 $m^2$, about 0.40 $m^2$ to about 10 $m^2$, about 0.45 $m^2$ to about 10 $m^2$, about 0.50 $m^2$ to about 10 $m^2$, about 0.55 $m^2$ to about 10 $m^2$, about 0.60 $m^2$ to about 10 $m^2$, about 0.65 $m^2$ to about 10 $m^2$, about 0.70 $m^2$ to about 10 $m^2$, about 0.75 $m^2$ to about 10 $m^2$, about 0.80 $m^2$ to about 10 $m^2$, about 0.85 $m^2$ to about 10 $m^2$, about 0.90 $m^2$ to about 10 $m^2$, about 0.95 $m^2$ to about 10 $m^2$, about 1.0 $m^2$ to about 10 $m^2$, about 1.1 $m^2$ to about 10 $m^2$, about 1.2 $m^2$ to about 10 $m^2$, about 1.3 $m^2$ to about 10 $m^2$, about 1.4 $m^2$ to about 10 $m^2$, about 1.5 $m^2$ to about 10 $m^2$, about 1.6 $m^2$ to about 10 $m^2$, about 1.7 $m^2$ to about 10 $m^2$, about 1.8 $m^2$ to about 10 $m^2$, about 1.9 $m^2$ to about 10 $m^2$, about 2.0 $m^2$ to about 10 $m^2$, about 2.1 $m^2$ to about 10 $m^2$, about 2.2 $m^2$ to about 10 $m^2$, about 2.3 $m^2$ to about 10 $m^2$, about 2.4 $m^2$ to about 10 $m^2$, about 2.5 $m^2$ to about 10 $m^2$, about 3.0 $m^2$ to about 10 $m^2$, about 3.5 $m^2$ to about 10 $m^2$, about 4.0 $m^2$ to about 10 $m^2$, about 4.5 $m^2$ to about 10 $m^2$, about 5.0 $m^2$ to about 10 $m^2$, about 6.0 $m^2$ to about 10 $m^2$, about 6.5 $m^2$ to about 10 $m^2$, about 7.0 $m^2$ to about 10 $m^2$, about 7.5 $m^2$ to about 10 $m^2$, about 8.0 $m^2$ to about 10 $m^2$, about 8.5 $m^2$ to about 10 $m^2$, about 9.0 $m^2$ to about 10 $m^2$, about 9.5 $m^2$ to about 10 $m^2$, about or 10 $m^2$.

In various embodiments, depending on the configuration (i.e., a parallel or serial configuration) one or more TFF cassettes and/or hollow fiber cartridges comprise an effective membrane area of about 0.01 $m^2$, about 0.01 $m^2$ to about 0.015 $m^2$, about 0.01 $m^2$ to about 0.02 $m^2$, about 0.01 $m^2$ to about 0.025 $m^2$, about 0.01 $m^2$ to about 0.03 $m^2$, about 0.01 $m^2$ to about 0.035 $m^2$, about 0.01 $m^2$ to about 0.04 $m^2$, about 0.01 $m^2$ to about 0.045 $m^2$, about 0.01 $m^2$ to about 0.05 $m^2$, about 0.01 $m^2$ to about 0.055 $m^2$, about 0.01 $m^2$ to about 0.06 $m^2$, about 0.01 $m^2$ to about 0.065 $m^2$, about 0.01 $m^2$ to about 0.07 $m^2$, about 0.01 $m^2$ to about 0.075 $m^2$, about 0.01 $m^2$ to about 0.08 $m^2$, about 0.01 $m^2$ to about 0.085 $m^2$, about 0.01 $m^2$ to about 0.09 $m^2$, about 0.01 $m^2$ to about 0.095 $m^2$, about 0.01 $m^2$ to about 0.1 $m^2$, about 0.01 $m^2$ to about 0.11 $m^2$, about 0.01 $m^2$ to about 0.12 $m^2$, about 0.01 $m^2$ to about 0.13 $m^2$, about 0.01 $m^2$ to about 0.14 $m^2$, about 0.01 $m^2$ to about 0.15 $m^2$, about 0.01 $m^2$ to about 0.16 $m^2$, about 0.01 $m^2$ to about 0.17 $m^2$, about 0.01 $m^2$ to about 0.18 $m^2$, about 0.01 $m^2$ to about 0.19 $m^2$, about 0.01 $m^2$ to about 0.20 $m^2$, about 0.01 $m^2$ to about 0.21 $m^2$, about 0.01 $m^2$ to about 0.22 $m^2$, about 0.01 $m^2$ to about 0.23 $m^2$, about 0.01 $m^2$ to about 0.24 $m^2$, about 0.01 $m^2$ to about 0.25 $m^2$, about 0.01 $m^2$ to about 0.26 $m^2$, about 0.01 $m^2$ to about 0.27 $m^2$, about 0.01 $m^2$ to about 0.28 $m^2$, about 0.01 $m^2$ to about 0.29 $m^2$, about 0.01 $m^2$ to about 0.30 $m^2$, about 0.01 $m^2$ to about 0.31 $m^2$, about 0.01 $m^2$ to about 0.32 $m^2$, about 0.01 $m^2$ to about 0.33 $m^2$, about 0.01 $m^2$ to about 0.34 $m^2$, about 0.01 $m^2$ to about 0.35 $m^2$, about 0.01 $m^2$ to about 0.40 $m^2$, about 0.01 $m^2$ to about 0.45 $m^2$, about 0.01 $m^2$ to about 0.50 $m^2$, about 0.01 $m^2$ to about 0.55 $m^2$, about 0.01 $m^2$ to about 0.60 $m^2$, about 0.01 $m^2$ to about 0.65 $m^2$, about 0.01 $m^2$ to about 0.70 $m^2$, about 0.01 $m^2$ to about 0.75 $m^2$, about 0.01 $m^2$ to about 0.80 $m^2$, about 0.01 $m^2$ to about 0.85 $m^2$, about 0.01 $m^2$ to about 0.90 $m^2$, about 0.01 $m^2$ to about 0.95 $m^2$, about 0.01 $m^2$ to about 1.0 $m^2$, about 0.01 $m^2$ to about 1.1 $m^2$, about 0.01 $m^2$ to about 1.2 $m^2$, about 0.01 $m^2$ to about 1.3 $m^2$, about 0.01 $m^2$ to about 1.4 $m^2$, about 0.01 $m^2$ to about 1.5 $m^2$, about 0.01 $m^2$ to about 1.6 $m^2$, about 0.01 $m^2$ to about 1.7 $m^2$, about 0.01 $m^2$ to about 1.8 $m^2$, about 0.01 $m^2$ to about 1.9 $m^2$, about 0.01 $m^2$ to about 2.0 $m^2$, about 0.01 $m^2$ to about 2.1 $m^2$, about 0.01 $m^2$ to about 2.2 $m^2$, about 0.01 $m^2$ to about 2.3 $m^2$, about 0.01 $m^2$ to about 2.4 $m^2$, about 0.01 $m^2$ to about 2.5 $m^2$, about 0.01 $m^2$ to about 3.0 $m^2$, about 0.01 $m^2$ to about 3.5 $m^2$, about 0.01 $m^2$ to about 4.0 $m^2$, about 0.01 $m^2$ to about 4.5 $m^2$, about 0.01 $m^2$ to about 5.0 $m^2$, about 0.01 $m^2$ to about 6.0 $m^2$, about 0.01 $m^2$ to about 6.5 $m^2$, about 0.01 $m^2$ to about 7.0 $m^2$, about 0.01 $m^2$ to about 7.5 $m^2$, about 0.01 $m^2$ to about 8.0 $m^2$, about 0.01 $m^2$ to about 8.5 $m^2$, about 0.01 $m^2$ to about 9.0 $m^2$, about 0.01 $m^2$ to about 9.5 $m^2$, about or 10 $m^2$.

In some embodiments, depending on the configuration (i.e., a parallel or serial configuration), the TFF cassettes and/or hollow fiber cartridges comprise an effective membrane area of 0.01 $m^2$, 0.015 $m^2$, 0.02 $m^2$, 0.025 $m^2$, 0.03 $m^2$, 0.035 $m^2$, 0.04 $m^2$, 0.045 $m^2$, 0.05 $m^2$, 0.055 $m^2$, 0.06 $m^2$, 0.065 $m^2$, 0.07 $m^2$, 0.075 $m^2$, 0.08 $m^2$, 0.085 $m^2$, 0.09 $m^2$, 0.095 $m^2$, 0.1 $m^2$, 0.11 $m^2$, 0.12 $m^2$, 0.13 $m^2$, 0.14 $m^2$, 0.15 $m^2$, 0.16 $m^2$, 0.17 $m^2$, 0.18 $m^2$, 0.19 $m^2$, 0.20 $m^2$, 0.21 $m^2$, 0.22 $m^2$, 0.23 $m^2$, 0.24 $m^2$, 0.25 $m^2$, 0.26 $m^2$, 0.27 $m^2$, 0.28 $m^2$, 0.29 $m^2$, 0.30 $m^2$, 0.31 $m^2$, 0.32 $m^2$, 0.33 $m^2$, 0.34 $m^2$, 0.35 $m^2$, 0.40 $m^2$, 0.45 $m^2$, 0.50 $m^2$, 0.55 $m^2$, 0.60 $m^2$, 0.65 $m^2$, 0.70 $m^2$, 0.75 $m^2$, 0.80 $m^2$, 0.85 $m^2$, 0.90 $m^2$, 0.95 $m^2$, 1.0 $m^2$, 1.1 $m^2$, 1.2 $m^2$, 1.3 $m^2$, 1.4 $m^2$, 1.5 $m^2$, 1.6 $m^2$, 1.7 $m^2$, 1.8 $m^2$, 1.9 $m^2$, 2.0 $m^2$, 2.1 $m^2$, 2.2 $m^2$, 2.3 $m^2$, 2.4 $m^2$, 2.5 $m^2$, 3.0 $m^2$, 3.5 $m^2$, 4.0 $m^2$, 4.5 $m^2$, 5.0 $m^2$, 6.0 $m^2$, 6.5 $m^2$, 7.0 $m^2$, 7.5 $m^2$, 8.0 $m^2$, 8.5 $m^2$, 9.0 $m^2$, 9.5 $m^2$, or 10 $m^2$.

Membranes (e.g., flat sheet or hollow fiber) suitable for use in particular embodiments contemplated herein may be made of a variety of different substrates or polymers known in the art. For example, in some embodiments, the TFF cassettes or hollow fiber cartridges comprise membrane(s) made of polysulfone, polyethersulfone, poly(methyl methacrylate), polyvinylidene fluoride, modified cellulose, regenerated cellulose, delta regenerated cellulose, cellulose acetate, and/or other polymers or substrates known to those skilled in the art. In some embodiments, the membrane is a polysulfone membrane. In some embodiments, the membrane is a polyethersulfone membrane. In some embodiments, the membrane is a poly(methyl methacrylate) membrane. In some embodiments, the membrane is a polyvinylidene fluoride membrane. In some embodiments, the membrane is a modified cellulose membrane. In some embodiments, the membrane is a regenerated cellulose membrane. In some embodiments, the membrane is a delta regenerated cellulose membrane. In some embodiments, the membrane is a cellulose acetate membrane.

In various embodiments, a membrane comprises an average molecular weight cut-off (MWCO) of about 1 kDa, about 5 kDa, about 10 kDa, about 20 kDa, about 30 kDa, about 40 kDa, about 50 kDa, about 60 kDa, about 70 kDa, about 80 kDa, about 90 kDa, about 100 kDa, about 200 kDa, about 300 kDa, about 400 kDa, or about 500 kDa. In some embodiments, the membrane comprises an average molecular weight cut-off (MWCO) of about 30 kDa. In some embodiments, the membrane comprises an average molecular weight cut-off (MWCO) of about 300 kDa.

In some embodiment, the membrane comprises an average molecular weight cut-off (MWCO) of about 1 kDa to about 500 kDa. In some embodiment, the membrane comprises an average MWCO of about 5 kDa to about 500 kDa. In some embodiment, the membrane comprises an average MWCO of about 10 kDa to about 500 kDa. In some embodiment, the membrane comprises an average MWCO of about 20 kDa to about 500 kDa. In some embodiment, the membrane comprises an average MWCO of about 30 kDa to about 500 kDa. In some embodiment, the membrane comprises an average MWCO of about 40 kDa to about 500 kDa. In some embodiment, the membrane comprises an average MWCO of about 50 kDa to about 500 kDa. In some embodiment, the membrane comprises an average MWCO of about 60 kDa to about 500 kDa. In some embodiment, the membrane comprises an average MWCO of about 70 kDa to about 500 kDa. In some embodiment, the membrane comprises an average MWCO of about 80 kDa to about 500 kDa. In some embodiment, the membrane comprises an average MWCO of about 90 kDa to about 500 kDa. In some embodiment, the membrane comprises an average MWCO of about 100 kDa to about 500 kDa. In some embodiment, the membrane comprises an average MWCO of about 200 kDa to about 500 kDa. In some embodiment, the membrane comprises an average MWCO of about 300 kDa to about 500 kDa. In some embodiment, the membrane comprises an average MWCO of about 400 kDa to about 500 kDa.

In some embodiment, the membrane comprises an average MWCO of about 1 kDa to about 5 kDa. In some embodiment, the membrane comprises an average MWCO of about 1 kDa to about 10 kDa. In some embodiment, the membrane comprises an average MWCO of about 1 kDa to about 20 kDa. In some embodiment, the membrane comprises an average MWCO of about 1 kDa to about 30 kDa. In some embodiment, the membrane comprises an average MWCO of about 1 kDa to about 40 kDa. In some embodiment, the membrane comprises an average MWCO of about 1 kDa to about 50 kDa. In some embodiment, the membrane comprises an average MWCO of about 1 kDa to about 60 kDa. In some embodiment, the membrane comprises an average MWCO of about 1 kDa to about 70 kDa. In some embodiment, the membrane comprises an average MWCO of about 1 kDa to about 80 kDa. In some embodiment, the membrane comprises an average MWCO of about 1 kDa to about 90 kDa. In some embodiment, the membrane comprises an average MWCO of about 1 kDa to about 100 kDa. In some embodiment, the membrane comprises an average MWCO of about 1 kDa to about 200 kDa. In some embodiment, the membrane comprises an average MWCO of about 1 kDa to about 300 kDa. In some embodiment, the membrane comprises an average MWCO of about 1 kDa to about 400 kDa. In some embodiment, the membrane comprises an average MWCO of about 1 kDa to about 500 kDa.

In various embodiments, a membrane comprises an average pore size of about 0.01 μm, about 0.02 μm, about 0.03 μm, about 0.04 μm, about 0.05 μm, about 0.06 μm, about 0.07 μm, about 0.08 μm, about 0.09 μm, about 0.1 μm, about 0.15 μm, about 0.2 μm, about 0.25 μm, about 0.3 μm, about 0.35 μm, about 0.4 μm, about 0.45 μm, about 0.5 μm, about 0.55 μm, about 0.6 μm, about 0.65 μm, about 0.7 μm, about 0.75 μm, about 0.8 μm, about 0.85 μm, about 0.9 μm, about 0.95 μm, or about 1.0 μm. In various embodiments, a membrane comprises an average pore size of 0.01 μm, 0.02 μm, 0.03 μm, 0.04 μm, 0.05 μm, 0.06 μm, 0.07 μm, 0.08 μm, 0.09 μm 0.1 μm, 0.15 μm, 0.2 μm, 0.25 μm, 0.3 μm, 0.35 μm, 0.4 μm, 0.45 μm, 0.5 μm, 0.55 μm, 0.6 μm, 0.65 μm, 0.7 μm, 0.75 μm, 0.8 μm, 0.85 μm, 0.9 μm, 0.95 μm, or 1.0 μm.

In various embodiments, a membrane comprises an average pore size of about 0.01 μm to about 1.0 μm, about 0.02 μm to about 1.0 μm, about 0.03 μm to about 1.0 μm, about 0.04 μm to about 1.0 μm, about 0.05 μm to about 1.0 μm, about 0.06 μm to about 1.0 μm, about 0.07 μm to about 1.0 μm, about 0.08 μm to about 1.0 μm, about 0.09 μm to about 1.0 μm, about 0.1 μm to about 1.0 μm, about 0.15 μm to about 1.0 μm, about 0.2 μm to about 1.0 μm, about 0.25 μm to about 1.0 μm, about 0.3 μm to about 1.0 μm, about 0.35 μm to about 1.0 μm, about 0.4 μm to about 1.0 μm, about 0.45 μm to about 1.0 μm, about 0.5 μm to about 1.0 μm, about 0.55 μm to about 1.0 μm, about 0.6 μm to about 1.0 μm, about 0.65 μm to about 1.0 μm, about 0.7 μm to about 1.0 μm, about 0.75 μm to about 1.0 μm, about 0.8 μm to about 1.0 μm, about 0.85 μm to about 1.0 μm, about 0.9 μm to about 1.0 μm, or about 0.95 μm to about 1.0 μm.

In various embodiments, a membrane comprises an average pore size of about 0.01 μm to about 0.02 μm, about 0.01 μm to about 0.03 μm, about 0.01 μm to about 0.04 μm, about 0.01 μm to about 0.05 μm, about 0.01 μm to about 0.06 μm, about 0.01 μm to about 0.07 μm, about 0.01 μm to about 0.08 μm, about 0.01 μm to about 0.09 μm, about 0.01 μm to about 0.1 μm, about 0.01 μm to about 0.15 μm, about 0.01 μm to about 0.2 μm, about 0.01 μm to about 0.25 μm, about 0.01 μm to about 0.3 μm, about 0.01 μm to about 0.35 μm, about 0.01 μm to about 0.4 μm, about 0.01 μm to about 0.45 μm, about 0.01 μm to about 0.5 μm, about 0.01 μm to about 0.55 μm, about 0.01 μm to about 0.6 μm, about 0.01 μm to about 0.65 μm, about 0.01 μm to about 0.7 μm, about 0.01 μm to about 0.75 μm, about 0.01 μm to about 0.8 μm, about 0.01 μm to about 0.85 μm, about 0.01 μm to about 0.9 μm, about 0.01 μm to about 0.95 μm, or about 0.01 μm to about 1.0 μm.

In some embodiments, a membrane is a microfiltration membrane.

In some embodiments, a membrane is an ultrafiltration membrane.

In some embodiments, a membrane is a nanofiltration membrane.

Exemplary TFF cassettes that are useful for the methods contemplated in particular embodiments herein include, but are not limited to, TFF cassettes supplied by MilliporeSigma Corporation (Burlington, Mass.), Pall Corporation (Port Washington, N.Y.), GE Healthcare Bio-Sciences (Piscataway, N.J.), and Sartorius AG (Bohemia, N.Y.) Exemplary MilliporeSigma Corporation TFF cassettes include, but are not limited to, Pellicon® cassettes (e.g., Pellicon® 2 cassettes, Pellicon® 2 Mini cassettes, Pellicon® 2 Maxi cassettes, Pellicon® 3 cassettes) with Biomax™ membrane, Ultracel™ membrane or Durapore® membrane. Exemplary Pall Corporation TFF cassettes include, but are not limited to Centrasette™ cassettes and Cadence™ single-use cassettes. Exemplary GE Healthcare Bio-Sciences TFF cassettes include, but are not limited to, Kvick™ Flow cassettes. Exemplary Sartorius AG cassettes include, but are not limited to, Hydrosart® cassettes.

An end plate or cassette holder is generally used to hold, or seal, the TFF cassettes in the SPTFF filtration module. The end plates and cassette holders can be fitted for use with particular cassettes. Examples of commercially-available end plates and cassette holders that are suitable for use in the SPTFF systems employed in the methods contemplated in particular embodiments herein include, but are not limited to, Pellicon® cassette holders (MilliporeSigma Corporation, Burlington, Mass.) such as, for example, Pellicon® 2 mini-holders, acrylic Pellicon® holders, stainless steel Pellicon® holders, process scale Pellicon® holders. Other suitable cassette holders include, but are not limited to, Centramate™ TFF membrane cassette holders, Centrasette™ TFF membrane cassette holders, Maximate™ TFF membrane cassette holders and Maxisette™ TFF membrane cassette holders (Pall Corporation, Port Washington, N.Y.). In some embodiments, existing cassette holders (e.g., Pellicon® cassette holders (Millipore Sigma Corporation)) can be modified to function in the SPTFF systems described herein for use in particular embodiments.

Exemplary hollow fiber TFF cartridges useful in particular embodiments contemplated herein include, but are not limited to, hollow fiber cartridges supplied by Pall Corporation (Port Washington, N.Y.), GE Healthcare Bio-Sciences (Piscataway, N.J.), and Repligen Corporation (Waltham, M.A.). Exemplary Pall Corporation hollow fiber cartridges include, but are not limited to Microza™ cartridges. Exemplary GE Healthcare Bio-Sciences hollow fiber TFF cartridges include, but are not limited to, MaxCell™ cartridges, ProCell™ cartridges, MidGee™ cartridges, Xampler™ cartridges, ReadyToProcess™ single-use cartridges, and various other laboratory and process scale cartridges. Exemplary Repligen Corporation hollow fiber cartridges include, but are not limited to, MicroKros™, MidiKros™, MidiKros TC™, MiniKros™, KrosFlo™, or KrosFlow Max™ cartridges.

In various embodiments, SPTFF system components can be disposable. Exemplary disposable components for SPTFF assemblies include, but are not limited to, components of Flexware® assemblies for Mobius® FlexReady Solution for TFF (MilliporeSigma Corporation, Burlington, Mass.). Other disposable components for SPTFF assemblies include, for example, components of Allegro™ TFF assemblies (Pall Corporation, Port Washington, N.Y.).

Without wishing to be bound by any particular theory, it is contemplated that one advantage of the SPTFF systems and methods contemplated herein is the surprising discovery that a low transmembrane pressure (TMP) improves (e.g., increases) volumetric and product concentration factors (VCF and PCF, respectively).

The term "transmembrane pressure" or "TMP" refers to the difference in pressure between two sides of a membrane. TMP pressure can be measured, for example, in atmospheric bars or pounds per square inch (psi). An average TMP can be calculated by dividing the sum of the feed pressure entering into an SPTFF filtration module and the retentate pressure exiting the SPTFF filtration module by two; and subtracting the permeate pressure. TMP=feed pressure+retentate pressure)/2−permeate pressure.

The term "volumetric concentration factor" or "VCF" refers to the fold change (e.g., reduction) in volume. VCF can be calculated by divided the initial composition volume by the final composition volume. VCF=initial volume/final volume.

The terms “product concentration factor”, “product CF”, “PCF”, “particle concentration factor”, or “viral particle concentration factor” refers to the fold change (e.g., increase) in product concentration (e.g., viral particle concentration). PCF can be calculated by dividing the final product concentration by the initial product concentration. PCT=final product concentration/initial product concentration.

In various embodiments, SPTFF filtration modules comprise a TMP of about 10 psi or lower, about 9 psi or lower, about 8 psi or lower, about 7 psi or lower, about 6 psi or lower, about 5 psi or lower, about 4 psi or lower, about 3 psi or lower, or about 2 psi or lower.

In some embodiments, the SPTFF filtration modules comprise an average TMP of about 10 psi or lower. In some embodiments, the SPTFF filtration modules comprise an average TMP of about 9 psi or lower. In some embodiments, the SPTFF filtration modules comprise an average TMP of about 8 psi or lower. In some embodiments, the SPTFF filtration comprise an average TMP of about 7 psi or lower. In some embodiments, the SPTFF filtration modules comprise an average TMP of about 6 psi or lower. In some embodiments, the SPTFF filtration modules comprise an average TMP of about 5 psi or lower. In some embodiments, the SPTFF filtration modules comprise an average TMP of about 4 psi or lower. In some embodiments, the SPTFF filtration modules comprise an average TMP of about 3 psi or lower. In some embodiments, the SPTFF filtration modules comprise an average TMP of about 2 psi or lower.

In some embodiments, the SPTFF filtration modules comprise an average TMP of about 1 psi to about 10 psi. In some embodiments, the SPTFF filtration modules comprise an average TMP of about 1 psi to about 9 psi. In some embodiments, the SPTFF filtration modules comprise an average TMP of about 1 psi to about 8 psi. In some embodiments, the SPTFF filtration modules comprise an average TMP of about 1 psi to about 7 psi. In some embodiments, the SPTFF filtration modules comprise an average TMP of about 1 psi to about 6 psi. In some embodiments, the SPTFF filtration modules comprise an average TMP of about 1 psi to about 5 psi. In some embodiments, the SPTFF filtration modules comprise an average TMP of about 1 psi to about 4 psi. In some embodiments, the SPTFF filtration modules comprise an average TMP of about 1 psi to about 3 psi. In some embodiments, the SPTFF filtration modules comprise an average TMP of about 1 psi to about 2 psi.

In some embodiments, the SPTFF filtration modules comprise an average TMP of about 2 psi to about 10 psi. In some embodiments, the SPTFF filtration modules comprise an average TMP of about 2 psi to about 9 psi. In some embodiments, the SPTFF filtration modules comprise an average TMP of about 2 psi to about 8 psi. In some embodiments, the SPTFF filtration modules comprise an average TMP of about 2 psi to about 7 psi. In some embodiments, the SPTFF filtration modules comprise an average TMP of about 2 psi to about 6 psi. In some embodiments, the SPTFF filtration modules comprise an average TMP of about 2 psi to about 5 psi. In some embodiments, the SPTFF filtration modules comprise an average TMP of about 2 psi to about 4 psi. In some embodiments, the SPTFF filtration modules comprise an average TMP of about 2 psi to about 3 psi.

E. Viral Vectors

In particular embodiments, SPTFF systems and related methods contemplated herein are used to manufacture purified and/or concentrated viral vectors. In particular embodiments, the composition comprises one or more viral vectors encoding a therapeutic transgene or protein, e.g., a globin or an engineered antigen receptor. Illustrative examples of viral vectors include, but are not limited to vectors derived from: an adenovirus, an adeno-associated virus (AAV), a retrovirus, e.g., a lentivirus (e.g., HIV-1, HIV-2), a herpes simplex virus e.g., HSV-1, HSV-2), anellovectors, or a vaccinia virus. In certain embodiments, the viral vector comprises a polynucleotide encoding a therapeutic transgene or therapeutic protein.

In various embodiments, the viral vector comprises a polynucleotide encoding a therapeutic protein. In various embodiments, the viral vector comprises a polynucleotide encoding an engineered αβ TCR, an engineered γδ TCR, a dimerizing agent regulated immunoreceptor complex (DARIC), a chimeric antigen receptor (CAR), a chimeric costimulatory receptor (CCR), a bispecific T cell engager (BiTE), a zetakine receptor, a chimeric TGFβ receptor (CTBR), a β-globin protein, an ABCD1 polypeptide, an erythropoietin receptor or fragment thereof, an endonuclease, or a megaTAL.

In various embodiments, a viral vector comprises a polynucleotide encoding a globin, a human globin, a human β-globin, a human δ-globin, a human γ-globin, a human anti-sickling β-globin, or a human $\beta^{A\text{-}T87Q}$-globin, a human $\beta^{A\text{-}G16D/E22NA/T87Q}$-globin, and a human $\beta^{A\text{-}T87Q/K95E/K120E}$-globin.

In particular embodiments, a therapeutic protein is an engineered antigen receptor that binds a target antigen selected from the group consisting of: alpha folate receptor (FRα), αvβ6 integrin, B cell maturation antigen (BCMA), B7-H3 (CD276), B7-H6, carbonic anhydrase IX (CAIX), CCR1, CD16, CD19, CD20, CD22, CD30, CD33, CD37, CD38, CD44, CD44v6, CD44v7/8, CD70, CD79a, CD79b, CD123, CD133, CD135 (also known as fmc like tyrosine kinase 3; FLT3), CD138, CD171, carcinoembryonic antigen (CEA), Claudin-6 (CLDN6), C-type lectin-like molecule-1 (CLL-1), CD2 subset 1 (CS-1), chondroitin sulfate proteoglycan 4 (CSPG4), cutaneous T cell lymphoma-associated antigen 1 (CTAGE1), epidermal growth factor receptor (EGFR), epidermal growth factor receptor variant III (EGFRvIII), epithelial glycoprotein 2 (EGP2), epithelial glycoprotein 40 (EGP40), epithelial cell adhesion molecule (EPCAM), ephrin type-A receptor 2 (EPHA2), fibroblast activation protein (FAP), Fc Receptor Like 5 (FCRLS), fetal acetylcholinesterase receptor (AchR), ganglioside G2 (GD2), ganglioside G3 (GD3), Glypican-3 (GPC3), EGFR family including ErbB2 (HER2), IL-11Rα, IL-13Rα2, Kappa, cancer/testis antigen 2 (LAGE-1A), Lambda, Lewis-Y (LeY), L1 cell adhesion molecule (L1-CAM), Leukocyte immunoglobulin-like receptor subfamily B member 2 (LILRB2); melanoma antigen gene (MAGE)-A1, MAGE-A3, MAGE-A4, MAGE-A6, MAGEA10, melanoma antigen recognized by T cells 1 (MelanA or MART1), Mesothelin (MSLN), MUC1, MUC16, neural cell adhesion molecule (NCAM), cancer/testis antigen 1 (NY-ESO-1), polysialic acid; placenta-specific 1 (PLAC1), preferentially expressed antigen in melanoma (PRAME), prostate stem cell antigen (PSCA), prostate-specific membrane antigen (PSMA), prostate-specific antigen (PSA), receptor tyrosine kinase-like orphan receptor 1 (ROR1), synovial sarcoma, X breakpoint 2 (SSX2), Survivin, tumor associated glycoprotein 72 (TAG72), T-cell immunoglobulin and mucin-domain containing-3 (TIM-3), TP53 (P53), tumor antigen p53, tumor endothelial marker 1 (tEM1/CD248), tumor endothelial marker 7-related (TEM7R), trophoblast glycoprotein (TPBG), NKG2D ligands, vascular endothelial growth factor receptor 2 (VEGFR2), and Wilms tumor 1 (WT-1).

In various embodiments, a viral vector comprises a polynucleotide encoding an shRNA, a shmiR, or a guide RNA. In some embodiments, the shRNA, shmiR, or guide RNA bind a target sequence in a BCL11A gene, e.g., a human BCL11A gene.

In various embodiments, viral vectors are produced by producer cells comprising the accessory proteins to package the vector into a viral particle. In some embodiments, the producer cells are maintained in suspension within a bioreactor. In some embodiments, the producer cells are adherent producer cells. In some embodiments, producer cells are HEK 293 cells. In some embodiments, the HEK 293 cells are HEK 293T or HEK 293F cells.

All publications, patent applications, and issued patents cited in this specification are herein incorporated by reference as if each individual publication, patent application, or issued patent were specifically and individually indicated to be incorporated by reference.

Although the foregoing embodiments have been described in some detail by way of illustration and example for purposes of clarity of understanding, it will be readily apparent to one of ordinary skill in the art in light of the teachings contemplated herein that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

Example 1

Single Pass Tangential Flow Filtration Systems

An illustrative single pass tangential flow filtration (SPTFF) system was assembled and tested. Specifically, modified HEK293T cells were cultured in a stirred-tank bioreactor until sufficient cell concentrations were reached. The cells cultures were perfused with induction media to induce lentiviral vector production. Cell culture medium containing lentiviral vector was continuously harvested from the bioreactor using alternating tangential flow filtration into a holding tank, pulling fresh media into the bioreactor to maintain a constant culture volume.

Figure 3:
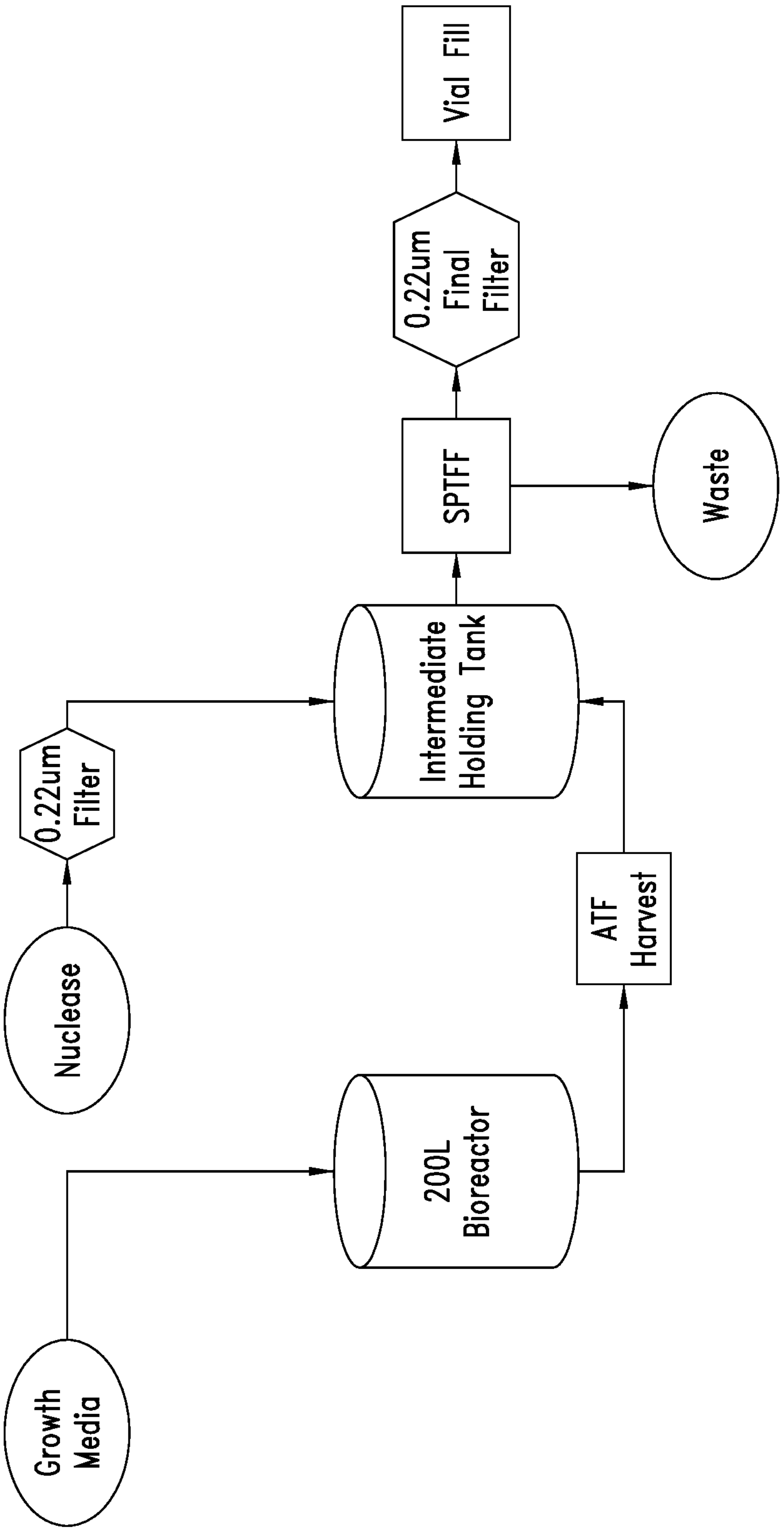
FIG. 3 shows an illustrative schematic of an SPTFF system.

Once sufficient lentiviral vector had been collected, the SPTFF filtration module comprising TFF cassettes assembled as shown in FIG. 1A, was primed and the harvested material was treated with nuclease to digest DNA impurities, as shown in FIG. 3. The material was slowly pumped into the SPTFF module, targeting a transmembrane pressure of 5 psi. Excess culture medium, devoid of lentiviral vector, was collected into a waste container from the permeate lines and concentrated lentiviral vector was collected from the retentate line. The concentrated lentiviral vector was then filtered using a 0.22 μm sterile filter to ensure sterility before vialing.

Figure 4:
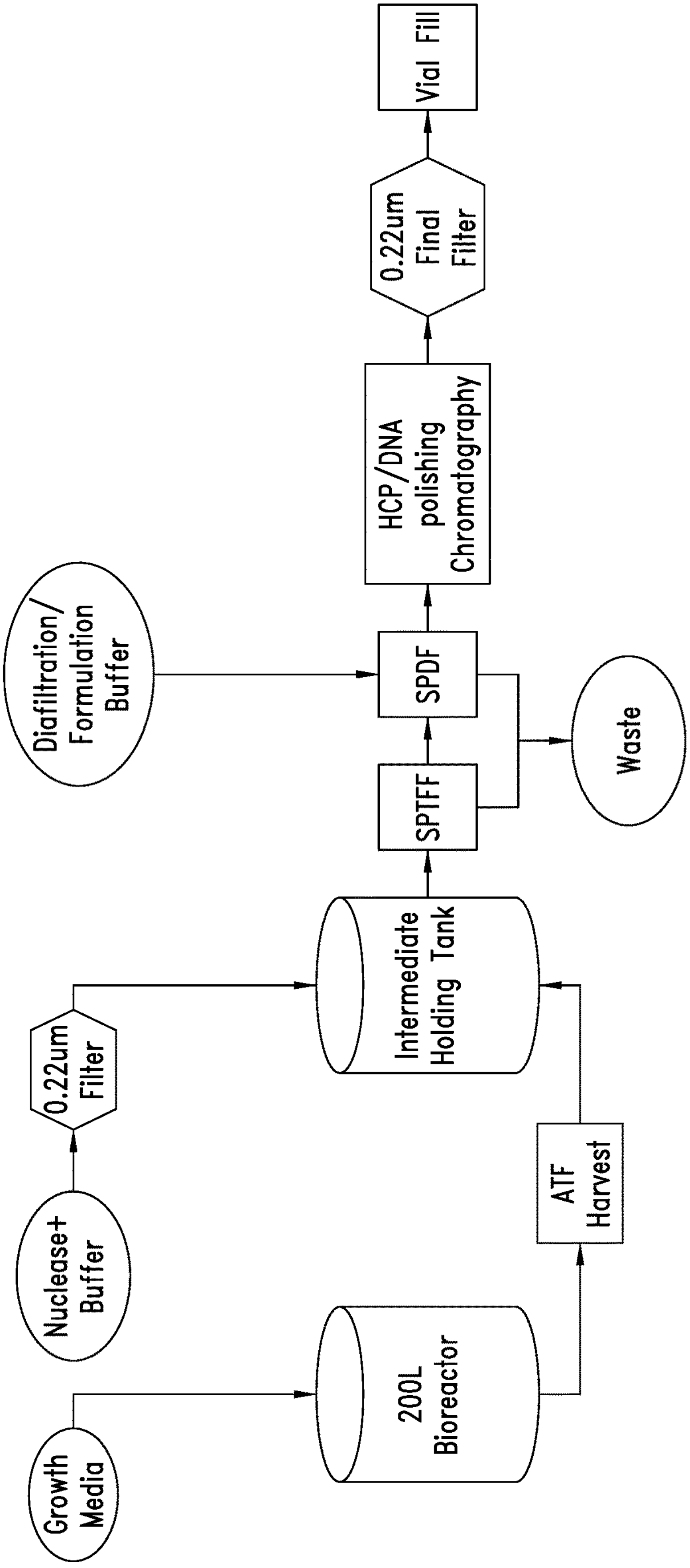
FIG. 4 shows an illustrative schematic of an SPTFF system having additional features and/or components.

Other SPTFF systems that were assembled and tested included additional diafiltration (e.g., using SPTFF and/or recirculating TFF) and polishing chromatography steps (e.g., size exclusion, hydrophobic interaction, and/or anion exchange chromatography) performed after SPTFF to further reduce unwanted impurities and properly formulate the lentiviral vector before final sterile filtration, as shown in FIG. 4.

Example 2

Use of an SPTFF System Improves Viral Vector Concentration, Purification, and Vector Copy Number Harvested cell culture medium containing lentiviral vector was collected from a stirred tank bioreactor containing modified HEK293 lentiviral vector producer cells. This material was then mixed thoroughly and split into several pools which were processed in parallel. Multiple pools were processed using the SPTFF purification process described in Example 1, while the final pool was processed using a standard vector purification process consisting of the following: clarification using a 0.45 μm filtration, capture chromatography, recirculated tangential flow filtration to perform ultrafiltration and diafiltration, and a final 0.22 μm sterile filtration.

Each final lentiviral vector product was then used to transduce CD34+ cells which were then cryopreserved. The transduced cells were thawed and cultured for 14 days before harvesting and performing qPCR to determine the total vector copy number (VCN) per cell.

Figure 5B:
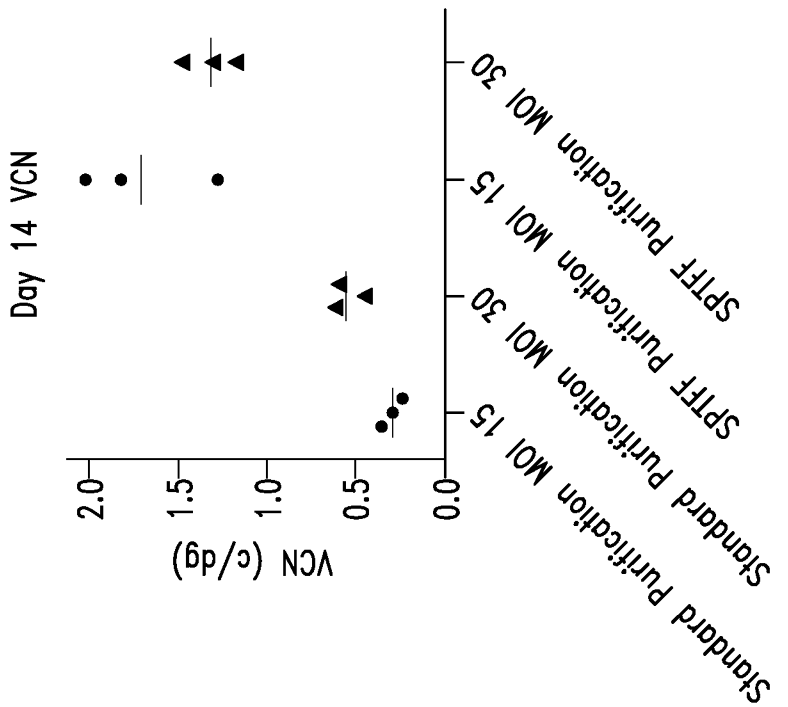
FIG. 5B is a graph depicting vector copy number (VCN) from cells transduced with concentrated lentiviral vectors produced using standard TFF and improved SPTFF systems/methods.
Figure 5A:
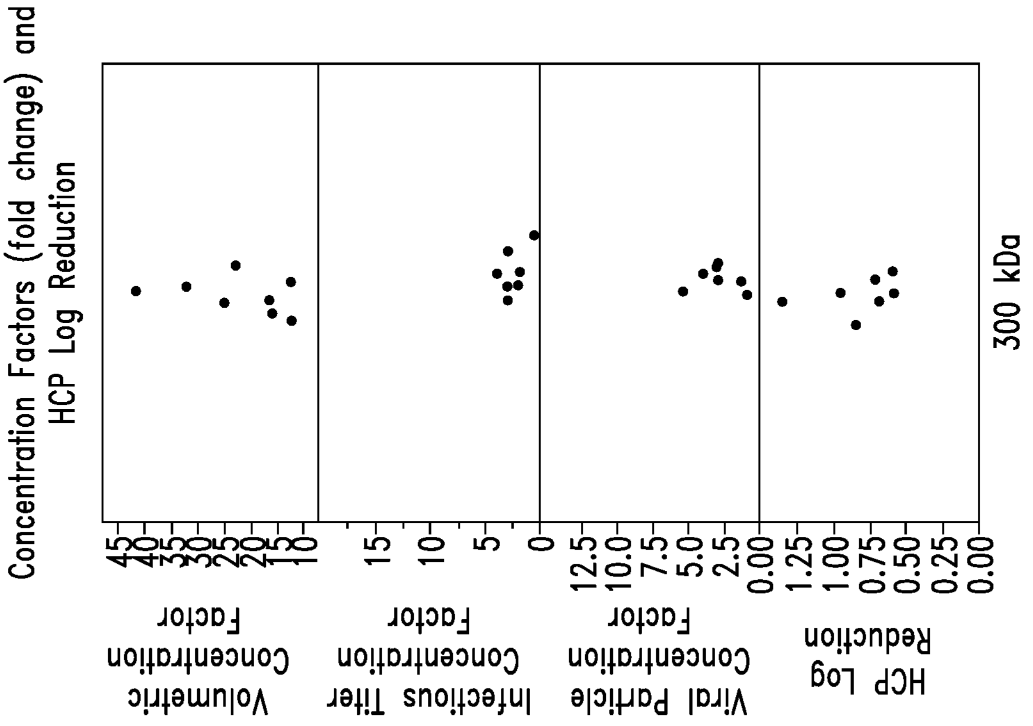
FIG. 5A is a graph depicting concentration factors (volumetric, titer, and particle) and host cell protein (HCP) levels for various experiments using 300 kDa membrane filters in an SPTFF system utilizing TFF cassettes.

As shown in FIG. 5A, the SPTFF process increased volumetric concentration, increased infectious titer (final titer/initial titer), increased viral particle concentration, and decreased host cell protein (HCP) levels. FIG. 5B, the SPTFF purification process increased the vector copy number of the drug product by 3-fold compared to the standard vector purification process.

Example 3

Decreasing Flow Rate Improves Volumetric and Product Concentration

Harvested cell culture medium containing lentiviral vector was collected from a stirred tank bioreactor containing modified HEK293 lentiviral vector producer cells. This material was thoroughly mixed throughout the duration of processing using SPTFF. The material was pumped into the SPTFF module, gradually ramping up the flow rate until material began flowing out the retentate line. The volumetric concentration factors and transmembrane pressures were then recorded at each flow rate tested, as shown in Table 1. The retentate pools were subsequently tested for lentiviral vector content and product concentration factors were retroactively calculated from those values.

Despite manufacturer recommendations to operate at higher flow rates to maximize transmembrane pressure and improve concentration factors, Table 1 shows that, surprisingly, volumetric concentration factors increased with slower flow rates and product concentration factors increased along with it, up to a certain point.

TABLE 1

| | Flow Rate (mL/min) | TMP (psi) | Volumetric Concentration Factor | Product Concentration Factor |
|---|---|---|---|---|
| Run 1 | 75 | 3.08 | 22.6 | 2.9 |
| Run 2 | 100 | 4.9 | 16.4 | 3.9 |
| Run 3 | 150 | 10.3 | 12.2 | 2.8 |

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method of purifying a viral vector composition comprising the steps of:

(a) feeding a composition comprising a viral vector through a single pass tangential flow filtration (SPTFF) system, the system comprising:

(i) a feed pump; and (ii) one or more SPTFF filtration modules, wherein the one or more SPTFF filtration modules purify the viral vector composition, and wherein the one or more SPTFF filtration modules have an average transmembrane pressure (TMP) of 2 psi±15% to 5 psi±15%; and (b) collecting a purified viral vector composition, wherein the system comprises a viral vector composition feed flow rate of 100 ml/min or less entering the one or more SPTFF filtration modules.

2. The method of claim 1, wherein the viral vector is a lentiviral vector.

3. The method of claim 1, wherein the SPTFF system does not comprise an affinity chromatography component or centrifugation.

4. The method of claim 1, wherein the one or more SPTFF filtration modules comprise three or more tangential flow filtration (TFF) cassettes or hollow fiber cartridges.

5. The method of claim 4, wherein: (i) the TFF cassettes comprise one or more flat sheet membranes, and/or (ii) the hollow fiber cartridges comprise one or more hollow fiber membranes.

6. The method of claim 5, wherein the one or more membranes comprises a molecular weight cut-off (MWCO) of about 30 kDa.

7. The method of claim 5, wherein the one or more membranes comprises an MWCO of about 300 kDa.

8. The method of claim 4, wherein the TFF cassettes or hollow fiber cartridges are configured for processing in parallel and/or serial.

9. The method of claim 8, wherein: (i) the viral vector composition follows a flow path through the SPTFF system and/or the one or more SPTFF filtration modules, (ii) the TFF cassettes or hollow fiber cartridges have an effective membrane area, and (iii) the effective membrane areas decreases along the flow path within the one or more SPTFF filtration modules.

10. The method of claim 1, wherein: the system comprises (a) a viral vector composition feed flow rate entering the one or more SPTFF filtration modules and (b) a viral vector composition retentate flow rate exiting the one or more SPTFF filtration modules, wherein the viral vector composition feed flow rate entering the one or more SPTFF filtration modules is at least 10× greater than the viral vector composition retentate flow rate exiting the one or more SPTFF filtration modules.

11. The method of claim 1, wherein the one or more SPTFF filtration modules have an average transmembrane pressure (TMP) of 2 psi to 5 psi.

12. The method of claim 1, wherein the feed pump is positioned before the one or more SPTFF filtration modules and continuous with the flow path.

13. The method of claim 12, wherein the system further comprises: (i) a retentate pump after the one or more SPTFF filtration modules and continuous with the flow path, and (ii) a waste or permeate pump.

14. The method of claim 13, wherein the viral vector composition is not recirculated through the SPTFF system, one or more SPTFF filtration modules, and/or any TFF cassettes or hollow fiber cartridges within the one or more SPTFF filtration modules.

15. The method of claim 1, wherein: (i) the system further comprises a single-pass diafiltration (SPDF) component following the one or more SPTFF filtration modules; (ii) the system further comprises a polishing chromatography component after the one or more SPTFF filtration modules, wherein the polishing chromatography component comprises a hydrophobic interaction resin, a size exclusion resin, and/or an ion exchange resin; and/or (iii) a 0.22 μm final filter.

16. The method of claim 15, wherein the polishing chromatography component comprises an anion exchange resin.

17. The method of claim 1, wherein the SPTFF system further comprises a mechanism to add a nuclease to the viral vector composition; and wherein a nuclease is added to the viral vector composition prior to feeding the viral vector composition through the one or more SPTFF filtration modules and/or after the viral vector composition has passed through the one or more SPTFF filtration modules.

18. The method of claim 17, wherein the nuclease is a DNA endonuclease.

19. The method of claim 1, wherein the system further comprises a bioreactor comprising viral vector producer cells in suspension.

* * * * *